United States Patent
Carre et al.

(10) Patent No.: US 12,109,248 B2
(45) Date of Patent: Oct. 8, 2024

(54) METHOD FOR ISOLATING AND DETECTING CANCER STEM CELLS

(71) Applicant: CARCIDIAG BIOTECHNOLOGIES, Gueret (FR)

(72) Inventors: Vincent Carre, Jabreille les Bordes (FR); Aurélie Lacroix, Panazol (FR)

(73) Assignee: Sylvain Gnaho, Bonneval (FR)

( * ) Notice: Subject to any disclaimer, the term of this patent is extended or adjusted under 35 U.S.C. 154(b) by 1066 days.

(21) Appl. No.: 16/979,062

(22) PCT Filed: Mar. 7, 2019

(86) PCT No.: PCT/FR2019/050516
§ 371 (c)(1),
(2) Date: Sep. 8, 2020

(87) PCT Pub. No.: WO2019/171010
PCT Pub. Date: Sep. 12, 2019

(65) Prior Publication Data
US 2021/0052697 A1    Feb. 25, 2021

(30) Foreign Application Priority Data
Mar. 8, 2018   (FR) ..................... 18/00202

(51) Int. Cl.
| | |
|---|---|
| A61K 38/16 | (2006.01) |
| A61K 47/54 | (2017.01) |
| A61K 47/69 | (2017.01) |
| C07K 14/42 | (2006.01) |
| C12N 5/095 | (2010.01) |
| G01N 33/574 | (2006.01) |

(52) U.S. Cl.
CPC .......... *A61K 38/168* (2013.01); *A61K 47/557* (2017.08); *A61K 47/6923* (2017.08); *C07K 14/42* (2013.01); *C12N 5/0695* (2013.01); *G01N 33/57484* (2013.01)

(58) Field of Classification Search
None
See application file for complete search history.

(56) References Cited

U.S. PATENT DOCUMENTS

| | | | | |
|---|---|---|---|---|
| 6,610,535 B1 * | 8/2003 | Lu | ........................ | C12N 5/0647 |
| | | | | 435/363 |
| 6,946,293 B1 * | 9/2005 | Lu | ........................ | C12N 5/0678 |
| | | | | 435/378 |
| 2009/0258792 A1 | 10/2009 | Wang et al. | | |

FOREIGN PATENT DOCUMENTS

| | | |
|---|---|---|
| WO | 2017/093696 | 6/2017 |
| WO | 2017/093697 | 6/2017 |
| WO | 2018/011474 | 1/2018 |
| WO | 2018/224761 | 12/2018 |

OTHER PUBLICATIONS

Tucker-Burden et al., Stem Cells and Development 21(13): 2374-2386 (Year: 2012).*
Roucka et al., Microarrays 5: S1 to S6 (Year: 2016).*
Cazet et al., "Tumour-associated carbohydrate antigens in breast cancer", Breast Cancer Research, Jan. 1, 2010, vol. 12, Article No. 204, XP055425990, 13 pages.
Rambaruth et al., "Cell surface glycan-lectin interactions in tumor metastasis", Acta Histochemica, Mar. 1, 2011, vol. 113, No. 6, pp. 591-600, XP028228118, 10 pages.
International Search Report for PCT/FR2019/050516 dated May 16, 2019, 7 pages, with English Translation.
Written Opinion of the ISA for PCT/FR2019/050516 dated May 16, 2019, 14 pages, with English Translation.
French Search Report for French Application No. 1800202 dated Aug. 16, 2018.
Bomken et al., "Understanding the cancer stem cell", British Journal of Cancer, 2010, vol. 103, pp. 439-445.
Brooks, "Lectin Histochemistry: Historical Perspectives, State of the Art, and the Future", Carlo Pellicciari and Marco Biggiogera (eds.), Histochemistry of Single Molecules: Methods and Protocols, Methods in Molecular Biology, 2017, vol. 1560, pp. 93-107.
Kim et al., "Protein immobilization techniques for microfluidic assays", Biomicrofluidics 7, 2013, 041501, pp. 041501-1-041501-47 (48 total pages).
Rini, "Lectin Structure", Annu. Rev. Biophys. Biomol. Struct., 1995, vol. 24, pp. 551-577.
Singh et al., "Insight of Lectins—A review", International Journal of Scientific & Engineering Research, Apr. 2012, vol. 3, Issue 4, pp. 1-9.
Tao et al., "Imagable 4TI model for the study of late stage breast cancer", BMC Cancer, 2008, vol. 8:228, pp. 1-19.
Velasco-Velázquez et al., "Breast Cancer Stem Cells", Cancer Stem Cells Theories and Practice, 2011, pp. 63-78 (17 total pages).

* cited by examiner

*Primary Examiner* — Phuong Huynh
(74) *Attorney, Agent, or Firm* — NIXON & VANDERHYE

(57) ABSTRACT

Disclosed is the in vitro use of at least one lectin for marking cancer stem cells of hormone-dependent cancer target organs, selected from the lectins *Maackia amurensis* lectin II (MAH-II), *Euonymus europaeus* lectin (EEL), *Psophocarpus tetragonolobus* lectin I (PTL-I) and *Griffonia simplicifolia* lectin II (GSL-II), in particular at least two lectins selected from MAH-II, EEL, PTL-I and GSL-II, in particular the two lectins MAH-II and EEL, in order to obtain cancer stem cells of labeled hormone-dependent cancer target organs in a biological sample.

6 Claims, 4 Drawing Sheets

A

B

A

B

METHOD FOR ISOLATING AND DETECTING CANCER STEM CELLS

CROSS-REFERENCE TO RELATED APPLICATIONS

This application is the U.S. national phase of International Application No. PCT/FR2019/050516 filed Mar. 7, 2019 which designated the U.S. and claims priority to French Application No. 18/00202 filed Mar. 8, 2018, the entire contents of each of which are hereby incorporated by reference.

BACKGROUND OF THE INVENTION

Field of the Invention

The present invention relates to a method of isolating and detecting cancer stem cells (CSCs) of hormone-dependent cancer target organs.

The hormone-dependent cancer target organs are in particular the breast, uterus, prostate, ovaries, endometrium, thyroid and adrenal glands.

Description of the Related Art

Breast cancer is the leading cause of cancer death in France in women. It affects 48,000 people per year. Nearly 12,000 people per year die from this pathology with about one in 10 women affected during her lifetime. The 5-year survival rate is very low in the context of metastasized breast cancer, hence the notion of early diagnosis which is involved in this pathology where the present invention takes on its full meaning (Velasco-Velazquez et al., 2011).

With nearly 3,000 new cases estimated in 2008 in France, cervical cancer is the eleventh cause of cancer in women. The peak incidence is at 40 years. Cervical cancer is responsible for nearly 1,000 deaths annually. The peak of mortality is at age 50. The majority of cervical cancers are carcinomas. Cervical cancer is, in the majority of cases, a disease of infectious origin that progresses slowly (HPV papillomavirus). With nearly 54,000 new cases estimated in France in 2011, prostate cancer is the most common cancer, both in men and in the general population. It is very rare before the age of 50 and its incidence gradually increases with age. The average age at diagnosis is almost 70 years.

Ovarian cancer is the seventh leading cause of cancer in women with an estimated 4,430 new cases in 2008. The median age at diagnosis is 65 years. The most important risk factor for ovarian cancer is genetic.

Endometrial cancer is the most frequent gynecological cancer in France, ranking 5th among cancers in women in terms of incidence with 6,560 new cases estimated in 2010. This cancer usually occurs after menopause. The average age of patients at diagnosis is 68 years. The main risk factors for endometrial cancer are obesity, diabetes and treatment with tamoxifen.

Thyroid cancers are rare: they represent only 2% of all cancers diagnosed each year in France, or just over 8,000 new cases per year. However, it is a steadily increasing disease: the frequency of thyroid cancer increased by 3 to 5% each year between 1980 and 2012. However, the disease has a good prognosis: there were 375 deaths in 2012, a figure that has been steadily decreasing for more than thirty years.

Cancer of the adrenal glands has an estimated annual incidence of 1 to 2 cases per million population. It most often occurs in adults between the ages of 40 and 50, but also in children under 15. This tumor is more often seen in women than in men, without knowing the reason.

Breast cancer like the other hormone-dependent cancer target organs present multiple factors inducing a high mortality rate within the population concerned, in particular with a late diagnosis, resulting in both a more advanced cancer known as metastatic but also a high recidivism rate. Indeed, this rate depends directly on the stage at which the cancer is detected. However, even when the detection stage is early, the recurrence rate remains high because certain parameters are not taken into account for the time being.

Indeed, this phenomenon of recurrence can be explained in part by tumor progression as well as by resistance mechanisms based on the existence of cancer stem cells or tumor initiating cells or pre-cancer cells, not taken into account at this day. The therapeutic escape of the tumor from radiotherapy and chemotherapy treatments depends on the presence of these cells within the tumor. Therefore, detecting these cells in tumor tissue is one way to define the level of tumor aggressiveness. The characterization of specific biomarkers of cancer stem cells is therefore of great diagnostic and prognostic interest in the treatment of cancer. However, there are currently no specific markers of cancer stem cells (CSCs) that allow them to be discriminated against with certainty from other tumor cells.

The major difficulties in isolating and characterizing CSCs lie in the small size of their population (3 to 4% of the tumor population) and the absence of specific markers. There is therefore a significant need for early diagnosis and the development of a new method for the detection and/or isolation of cancer stem cells (Bomken et al., 2010).

Early identification of the presence of cancer stem cells would provide clinicians with a predictor of the disease.

In addition, it would offer new perspectives in the diagnosis of cancer dangerousness.

In fact, the additional information available to the clinician should make it possible to limit the risk of recurrence or worsening of the disease by adjusting the treatment.

The establishment of new markers therefore appears to be of major importance in the targeted treatment of these pathologies (Tao et al., 2008).

SUMMARY OF THE INVENTION

The present invention relates to a specific method of detection since it recognizes only cancer stem cells of hormone-dependent cancer target organs and is therefore more efficient than conventional methods. In addition, its implementation is faster compared to existing methods, because the latter cannot be generalized due to their non-reproducibility and combine both stem and non-cancer stem cells. Hormone-dependent cancers are cancers sensitive to sex hormones. Hormone-dependent tumors mainly form in tissues whose functioning is normally regulated by hormones. The growth of tumors is stimulated by hormones, such as, for example, testosterone, a male sex hormone in the case of prostate cancer, or estrogen, a female sex hormone secreted by the ovaries, in the case of breast cancer.

By the expression "cancer stem cells from hormone-dependent cancer target organs" is meant cancer stem cells originating from organs in which oncogenic development can be impacted by the hormones present in these organs, but also cancer stem cells from these organs when oncogenic development is not impacted by hormones.

In other words, this corresponds to cancer stem cells originating from target organs of hormone-dependent cancers, but also to said cancer stem cells originating from said organs when the cancers affecting these organs are non-hormone-dependent (non-hormone-dependent cancers). The target organs of hormone-dependent cancers are organs under hormonal influence.

The ARC Foundation for Cancer Research and the National Cancer Institute give as examples of hormone-dependent cancers breast, uterine, prostate and ovarian, endometrial, thyroid and adrenal glands. Note that breast cancer is also called mammary cancer.

Thus, the target organs of hormone-dependent cancers are in particular the breast, uterus, prostate, ovaries, endometrium, thyroid and adrenal glands.

In most cases, cancers affecting these organs are hormone-dependent, that is, hormones play a role in the proliferation of cancer cells. However, in some cases, cancers affecting these organs are non-hormone-dependent, meaning the hormones have no effect on cancer cells.

Thus, the cancer stem cells of hormone-dependent cancer target organs isolated and detected by the present invention correspond to the cancer stem cells of these hormone-dependent cancer target organs, in the case where these organs are affected by hormone-dependent cancer but also in special cases where these organs are affected by a non-hormone-dependent cancer.

In a particular embodiment, the cancer stem cells of target organs of hormone-dependent cancers correspond to cancer stem cells of the breast, uterus, prostate, ovaries, endometrium, thyroid or adrenal glands, whether these organs are affected by hormone-dependent cancer or non-hormone-dependent cancer.

In the present application the expression "cancer stem cells of hormone-dependent cancer target organs" is equivalent to the expression "cancer stem cells of hormone-dependent cancers", and these two expressions are used interchangeably.

Thus, breast cancer is a typical example of hormone-dependent cancers. However, breast cancer can also be a type of non-hormone-dependent cancer. For example, and without limitation, triple negative breast cancer is a type of non-hormone-dependent breast cancer.

In a first aspect, the present invention relates to the use, as a labeling means, of a lectin, for the detection and/or isolation of cancer stem cells of hormone-dependent cancers.

In a second aspect, the present invention relates to a method of isolating and detecting cancer stem cells of hormone-dependent cancers comprising labeling cancer stem cells of hormone-dependent cancers with at least one lectin.

In a third aspect, the present invention relates to a method of diagnosing the aggressiveness and/or the risk of recurrence of a hormone-dependent cancer to define a prognostic value for the therapeutic adaptation of a hormone-dependent cancer comprising a stage of isolation and/or detection of cancer stem cells of hormone-dependent cancers.

In a fourth aspect, the present invention relates to a kit comprising a lectin for detecting or isolating cancer stem cells of hormone-dependent cancers.

For the purposes of the present invention, the term "means for labeling cancer stem cells of hormone-dependent cancers" is understood to mean a substance capable of binding specifically to a marker expressed on the surface of cancer stem cells of hormone-dependent cancers.

According to a general aspect, the present invention relates to the in vitro use of at least one lectin for the labeling of cancer stem cells of hormone-dependent cancer target organs, chosen from the lectins *Maackia amurensis* lectin II (MAH-II), *Euonymus europaeus* lectin (EEL), *Psophocarpus tetragonolobus* lectin I (PTL-I) and *Griffonia simplicifolia* lectin II (GSL-II), to obtain labeled cancer stem cells of hormone-dependent cancers, in a biological sample.

These lectins are well known to those skilled in the art and available commercially (in particular from Vector Laboratories and Emelca Biosciences). Reviews list their structure (Lectin Structure, Rini J M, Annu Rev Biophys Biomol Struct, 1995; 24: 551-77) while others more recent describe their entire history (Insight of Lectins-A review, Singh et al., International Journal of Scientific and Engineering Research, volume 3, issue 4, April 2012) and the in their use in particular in immunohistochemistry (*Lectin Histochemistry: Historical Perspectives, State of the Art, and the Future*, Brooks S A, Methods Mol Biol, 2017, 1560: 93-107).

MAH-II and PTL-I lectins recognize O-linked glycans present on the surface of cells. More particularly, the MAH-II lectin specifically recognizes the disialyl-T group [NeuAc α2-3Gal β1-3 (NeuAc α2-6) GalNAc] and the PTL-I lectin specifically recognizes the Gal α1-3 (Fuc α 1-2) Gal and GalNAc α 1-3 (Fuc α 1-2) Gal groups of antigens B and A.

The EEL lectin recognizes the galactosylated glycans present on the surface of cells. More specifically, the EEL lectin recognizes the Gal α 1-3 (Fuc α 1-2) Gal group of the B antigen and the Fuc α1-2Galβ 1-3GlcNAc group of the H antigen.

The GSL-II lectin recognizes N-linked glycans, in particular tri- or tetra-antennated agalactosylated N-linked glycans, ie without galactose.

In a particular embodiment, the present invention relates to the in vitro use of MAH-II lectin and/or EEL lectin to obtain labeled hormone-dependent cancer stem cells in a biological sample.

For the purposes of the present invention, the biological sample is a sample taken from a patient with hormone-dependent or non-hormone-dependent cancer or likely to have hormone-dependent or non-hormone-dependent cancer.

For the purposes of the invention, this sample can be a solid or liquid biopsy, smear, extemporaneous biopsies of a hormone-dependent cancer target organs.

The biological sample can thus correspond to a sample of a hormone-dependent cancer target organ, in the case where this organ is affected by a hormone-dependent cancer or is likely to be, but also in the case where this organ has or is likely to have non-hormone-dependent cancer.

The biological sample can thus correspond to a sample from the breast, uterus, prostate, ovaries, endometrium, thyroid or adrenal glands.

This sample is likely to contain cancer stem cells.

Unlike or in addition to the usual analyzes in anatomo-pathology, the use of lectins according to the present invention ultimately makes it possible to characterize said sample at an early stage, as being pre-tumoral or tumoral. By the term "pre-tumor" is meant upstream of the tumor with a potential which may or may not lead to a tumor character in G sample.

In fact, anatomo-pathology studies macroscopic and microscopic lesions of tissues taken from living beings that are sick or have died by biopsy, smear or extemporaneous biopsy. This branch of medicine thus focuses on the morphological study of macroscopic and microscopic abnormalities in biological tissues and pathological cells taken, but not in the search for cancer stem cells and therefore not on the self-replicating properties of cells.

The anatomo-pathology does not allow, based on morphological studies, to establish an early characterization of the sample because the observed abnormalities occur at a stage when the self-replicating nature of cancer cells is already expressed.

On the contrary, the present invention being directly attached to the detection of the presence of cancer stem cells, this makes it possible to characterize the sample at an earlier stage than the anatomo-pathology, that is to say even before the cancer stem cells. could express their self-replicating character leading to morphological abnormalities in the tissues.

The method according to the present invention can be implemented downstream of an anatomo-pathology analysis. In this case, the sample is characterized as tumoral, likely to be tumoral or not suspected of being tumoral following the anatomo-pathology study. The method according to the present invention being specifically interested in cancer stem cells, it makes it possible in this case to confirm the diagnosis obtained in anatomopathology, or to invalidate this diagnosis.

Indeed, in the case where a sample is not suspected of being tumoral in anatomopathology, the present invention can make it possible to invalidate this diagnosis by revealing the tumoral or pre-tumoral character of said sample because it is based on parameters other than anatomo-pathology, in this case the presence and possibly the quantification of cancer stem cells.

Thus, according to one embodiment, the invention relates to the in vitro use of at least one lectin for the labeling of cancer stem cells of hormone-dependent cancer target organs, chosen from *Maackia amurensis* lectin II (MAH-II), *Euonymus europaeus* lectin (EEL), *Psophocarpus tetragonolobus* lectin I (PTL-I) and *Griffonia simplicifolia* lectin II (GSL-II), to obtain labeled cancer stem cells of hormone-dependent cancer target organs, in a biological sample.

In particular at least two lectins chosen from MAH-II, EEL, PTL-I and GSL-II, in particular the two lectins MAH-II and EEL.

According to a particular embodiment, the present invention relates to the in vitro use of at least two lectins chosen from MAH-II, EEL, PTL-I and GSL-II.

According to one embodiment, the present invention relates to the in vitro use of two lectins selected from MAH-II, EEL, PTL-I and GSL-II.

Thus, in one embodiment, the present invention relates to the in vitro use of a mixture of two lectins chosen from the following mixtures: (MAH-II, EEL), (MAH-II, PTL-I), (MAH-II, GSL-II), (EEL, PTL-I), (EEL, GSL-II), (PTL-I, GSL-II).

In a particular embodiment, the present invention relates to the in vitro use of a mixture of the two lectins MAH-II and EEL, also denoted MAH-II/EEL.

For the entire application, a mixture of lectins noted for example (MAH-II/EEL) is equivalent to a mixture of lectins noted (MAH-II, EEL).

According to one embodiment, the present invention relates to the in vitro use, as described above, of at least two lectins, said at least two lectins being in equal quantity.

According to one embodiment, the present invention relates to the in vitro use of at least two lectins chosen from MAH-II, EEL, PTL-I and GSL-II lectins, said at least two lectins being in equal quantity.

According to one embodiment, the present invention relates to the in vitro use of a mixture of two lectins chosen from MAH-II, EEL, PTL-I and GSL-II lectins, said two lectins being in an equal quantity in said mixture.

By equal amount we mean that each of the two lectins is used in the same amount as the other. This is a 1:1 weight ratio between the two lectins.

Thus, in one embodiment, the present invention relates to the in vitro use of a mixture of two lectins chosen from the following mixtures: (MAH-II, EEL), (MAH-II, PTL-I), (MAH-II, GSL-II), (EEL, PTL-I), (EEL, GSL-II), (PTL-I, GSL-II), said two lectins being in equal quantity in said mixture.

According to one embodiment, the present invention relates to the in vitro use of two lectins, said two lectins being an mixture of MAH-II/EEL, in which each of the lectins are in equal quantity.

According to one embodiment, the present invention relates to the in vitro use, as described above, of at least two lectins, said at least two lectins being in unequal quantity.

According to one embodiment, the present invention relates to the in vitro use of at least two lectins chosen from MAH-II, EEL, PTL-I and GSL-II lectins, said at least two lectins being in unequal quantity.

According to one embodiment, the present invention relates to the in vitro use of a mixture of two lectins chosen from MAH-II, EEL, PTL-I and GSL-II lectins, said two lectins being in unequal quantity in said mixture.

By unequal amount, we mean that each of the lectins is present in different amounts compared to the other. In particular, this is a 2:1 weight ratio between the two lectins.

Thus, in one embodiment, the present invention relates to the in vitro use of a mixture of two lectins chosen from the following mixtures: (MAH-II, EEL), (EEL, MAH-II), (MAH-II, PTL-I), (PTL-1, MAH-II), (MAH-II, GSL-II), (GSL-II, MAH-II), (EEL, PTL-I), (PTL-I, EEL), (GSL-II, EEL), (EEL, GSL-II), (PTL-I, GSL-II), (GSL-II, PTL-I), said two lectins being in unequal quantity in said mixture, in especially in a weight ratio of 2:1.

According to a particular embodiment, the present invention relates to the in vitro use of two lectins, said two lectins being a mixture (MAH-II and EEL), in which the lectins are in unequal quantity in a ratio by weight of 2:1 or 2 MAH-II for 1 EEL.

Thus, according to one embodiment, the present invention relates to the in vitro use, as described above, of two lectins, said two lectins being in unequal quantity in a weight ratio of 2:1, in particular the use in vitro as described above of the two MAH-II/EEL lectins in a weight ratio of 2:1.

Thus, according to one embodiment, the present invention relates to the in vitro use, as described above, in which at least two lectins are used, said at least two lectins being in equal quantity or in unequal quantity, in particular in unequal amount in a 2:1 weight ratio, and preferably both lectins being MAH-II/EEL in unequal amount in a 2:1 weight ratio.

According to a particular embodiment, the present invention relates to the in vitro use of at least three lectins chosen from MAH-II, EEL, PTL-1 and GSL-II lectins.

According to one embodiment, the present invention relates to the in vitro use of three lectins selected from MAH-II, EEL, PTL-I and GSL-II.

Thus, in one embodiment, the present invention relates to the in vitro use of a mixture of three lectins chosen from the following mixtures: (MAH-II, EEL, PTL-I), (MAH-II, EEL, GSL-II), (EEL, PTL-I, GSL-II), (MAH-II, PTL-I, GSL-II).

According to one embodiment, the present invention relates to the in vitro use of at least three lectins chosen from MAH-II, EEL, PTL-I and GSL-II lectins, said at least three lectins being in equal quantity. According to one embodiment, the present invention relates to the in vitro use of a mixture of three lectins chosen from MAH-II, EEL, PTL-I and GSL-II lectins, said three lectins each being in an equal quantity in said mixed.

By equal amount is meant that each of the three lectins is used in the same amount compared to the others. This is a 1:1:1 weight ratio between the three lectins. Thus, according to one embodiment, the present invention relates to the in vitro use of a mixture of three lectins, chosen from the following mixtures: (MAH-II, EEL, PTL-I), (MAH-II, EEL, GSL-II), (EEL, PTL-1, GSL-II), (MAH-II, PTL-I, GSL-II), said three lectins being in equal quantity in said mixture.

According to one embodiment, the present invention relates to the in vitro use of at least three lectins selected from MAH-II, EEL, PTL-I and GSL-II lectins, said at least three lectins being in unequal quantity.

According to one embodiment, the present invention relates to the in vitro use of a mixture of three lectins chosen from MAH-II, EEL, PTL-I and GSL-II lectins, said three lectins being in unequal quantity in said mixture. In the case of the use of three lectins, by unequal quantity is meant that the three lectins are not used in equal quantity with respect to each other, and that at least two lectins out of the three are used in different quantities. In particular, this is a 2:1:1 weight ratio between the three lectins.

Thus, according to a particular embodiment, the present invention relates to the in vitro use of a mixture of three lectins chosen from the following mixtures: (MAH-II, EEL, PTL-I), (EEL, MAH-II, PTL-I), (PTL-I, MAH-II, EEL), (MAH-II, EEL, GSL-II), (EEL, MAH-II, GSL-II), (GSL-II, MAH-II, EEL), (EEL, GSL-II, PTL-I), (PTL-I, EEL, GSL-II), (GSL-II, EEL, PTL-I), said three lectins being in unequal quantity in said mixture, in particular in a weight ratio of 2:1:1.

According to a particular embodiment, the present invention relates to the in vitro use of the four lectins MAH-II, EEL, PTL-I and GSL-II.

According to a particular embodiment, the present invention relates to the in vitro use of a mixture of the four lectins MAH-II, EEL, PTL-I and GSL-II.

According to one embodiment, the present invention relates to the in vitro use of the four lectins MAH-II, EEL, PTL-I and GSL-II, said four lectins being in equal quantity.

According to one embodiment, the present invention relates to the in vitro use of a mixture of the four lectins MAH-II, EEL, PTL-I and GSL-II, said four lectins being in equal quantity in said mixture.

By equal amount is meant that each of the four lectins is used in the same amount compared to the others. This is a 1:1:1:1 weight ratio between the four lectins.

According to one embodiment, the present invention relates to the in vitro use of the four lectins MAH-II, EEL, PTL-I and GSL-II, said four lectins being in unequal quantity.

According to one embodiment, the present invention relates to the in vitro use of a mixture of the four lectins MAH-II, EEL, PTL-I and GSL-II, said four lectins being in unequal quantity in said mixture.

In the case of using four lectins, by unequal amount is meant that the four lectins are not used in equal amounts with respect to each other, and at least two of the four lectins are used in amounts different. In particular, this is a 2:1:1:1 weight ratio between the four lectins. Thus, according to a particular embodiment, the present invention relates to G use in vitro of a mixture of four lectins chosen from the following mixtures: (MAH-II, EEL, PTL-I, GSL-II), (MAH-II, EEL, GSL-II, PTL-I), (MAH-II, PTL-I, EEL, GSL-II), (MAH-II, PTL-I, GSL-II, EEL), (MAH-II, GSL-II, PTL-I, EEL), (MAH-II, GSL-II, EEL, PTL-I), (EEL, MAH-II, PTL-I, GSL-II), (EEL, MAH-II, GSL-II, PTL-I), (EEL, PTL-I, MAH-II, GSL-II), (EEL, PTL-I, GSL-II, MAH-II), (EEL, GSL-II, MAH-II, PTL-I), (EEL, GSL-II, PTL-I, MAH-II), (GSL-II, EEL, PTL-I, MAH-II), (GSL-II, EEL, MAH-II, PTL-I), (GSL-II, PTL-I, EEL, MAH-II), (GSL-II, PTL-I, MAH-II, EEL), (GSL-II, MAH-II, EEL, PTL-I), (GSL-II, MAH-II, PTL-I, EEL), (PTL-I, GSL-II, MAH-II, EEL), (PTL-I, GSL-II, EEL, MAH-II), (PTL-I, EEL, GSL-II, MAH-II), (PTL-I, EEL, MAH-II, GSL-II), (PTL-I, MAH-II, EEL, GSL-II), (PTL-I, MAH-II, GSL-II, EEL), said four lectins being in unequal amount in said mixture, in particular in a ratio by weight of 2:1:1:1.

The use of two, three or four lectins allows in some cases a better specificity of the labeling of cancer stem cells.

According to one embodiment, the present invention relates to the in vitro use, as described above, in which the MAH-II lectin recognizes O-linked glycans, in particular the disialyl-T group [NeuAc α2-3Gal β1-3 (NeuAc α2-6) GalNAc], the PTL-I lectin recognizes O-linked glycans, in particular the Gal α1-3 (Fuc α1-2) Gal and GalNAc α1-3 (Fuc α1-2) Gal groups of B and A antigens, the EEL lectin recognizes galactosylated glycans, in particular the Gal α1-3 (Fuc α1-2) Gal group of the B antigen and the Fuc α1-2Galβ1-3GlcNAc group of the H antigen, and the GSL-II lectin recognizes N-linked glycans, in particular N-linked tri- or tetra-antennal agalactosylated glycans.

According to one embodiment, the present invention relates to the in vitro use, as described above, in which said cancer is cancer of the breast, uterus, prostate and ovaries, endometrium, thyroid or adrenal glands.

The mixture in equal quantity of the two MAH-II/EEL lectins is an advantageous embodiment in the detection and isolation of CSCs from a hormone-dependent cancer, when said cancer is a hormone-dependent or non-hormone-dependent breast cancer.

The lectin used in the context of the invention can be conjugated.

For the purposes of the invention, by the term "conjugate" is meant that the lectin is covalently linked to another molecule.

According to one embodiment, the present invention relates to the in vitro use of at least one lectin chosen from MAH-II, EEL, PTL-I and GSL-II lectins, for the labeling of cancer stem cells of hormone-dependent cancers, wherein said labeling of cancer stem cells of hormone-dependent cancers is carried out with a lectin conjugated to a marker chosen from: a fluorophore, a radioisotope, an enzyme, gold beads or biotin.

Thus, in a particular embodiment, the lectin is conjugated to a fluorophore. For the purposes of the invention, a fluorophore can be any fluorophore capable of being used for flow cytometry. Such fluorophores are commercially available. This is for example the Alexa fluor, in particular the Alexa fluor 350, 405, 430, 488, 500, 514, 532, 546, 555, 568, 594, 610, 633, 647, 660, 680, 700, 750 or 790, fluorescein isothiocyanate (FITC), Rhodamine, allophycocyanin (APC) and Phycoerythrin (PE). Advantageously, the fluorophore is chosen from rhodamine, FITC or Alexa fluorine, in particular Alexa fluor 488, Alexa fluor 594 or Alexa fluor 633.

This characterization of the fluorophore within the meaning of the invention applies to any embodiment of the present invention involving a fluorophore.

In another particular embodiment, the lectin is conjugated to a radioisotope. For the purposes of the invention, a radioisotope is chosen from iodine 125, tritium or technetium.

In another particular embodiment, the lectin is conjugated to an enzyme.

Within the meaning of the invention, the enzyme is an enzyme catalyzing the formation of a colored product, that is to say an enzyme using a chromogenic substrate, or an enzyme catalyzing the formation of a luminescent product, that is to say that is, an enzyme using a chemiluminescent substrate.

For the purposes of the invention, a "chromogenic substrate" means a substrate giving a colored product after conversion by an enzyme. For the purposes of the invention, a "chemiluminescent substrate" means a substrate giving a luminescent product after conversion by an enzyme.

In a particular case of the invention, said enzyme catalyzing the formation of a colored product is chosen from horseradish peroxidase (HRP), alkaline phosphatase, glucose oxidase or β-galactosidase.

In the particular case of HRP, the chromogenic substrate is chosen from 3,3'-Diaminobenzidine (DAB), 3,3', 5,5'-Tetramethylbenzidine (TMB), or 2,2'-azino-bis (3-ethylbenzothiazoline-6-sulphonic acid) (ABTS).

In the particular case of alkaline phosphatase, the chromogenic substrate is NBT (tetrazolium nitroblue) and BCIP (bromochlorylindolophosphate).

In a particular case of the invention, said enzyme catalyzing the formation of a luminescent product is HRP and the luminescent substrate is luminol.

In another particular embodiment, the lectin is conjugated to gold beads.

In another particular embodiment, the lectin is conjugated to biotin. Thus, according to one embodiment, the present invention relates to the in vitro use, as described above, in which said labeling of cancer stem cells of hormone-dependent cancer target organs is carried out with a lectin conjugated to a. marker chosen from:
 a fluorophore in particular chosen from rhodamine, FITC or Alexa Fluor
 a radioisotope in particular chosen from iodine 125, tritium or technetium,
 an enzyme using a chromogenic or luminescent substrate, said enzyme being in particular chosen from horseradish peroxidase (HRP), alkaline phosphatase, glucose oxidase or β-galactosidase,
 gold beads or
 biotin.

It was also demonstrated by the inventors that the cancer stem cells of hormone-dependent cancers could be detected via the use of a lectin chosen from among the lectins MAH-II, EEL, PTL-I and GSL-II, for the labeling of said cancer stem cells of hormone-dependent cancers. For the purposes of the present invention, the term "detection" means the fact of identifying by UV/visible, luminescence, fluorescence, radioactivity and enzymology methods the presence of cancer stem cells of hormone-dependent cancers. within a biological sample.

Thus, the present invention also relates to the use of at least one lectin chosen from MAH-II, EEL, PTL-I and GSL-II lectins, for the labeling of cancer stem cells of hormone-dependent cancers followed by the detection. cancer stem cells in a biological sample, via the detection of said conjugated lectin.

In one embodiment, the lectin can be covalently conjugated to a fluorophore.

Thus, according to one embodiment, the present invention relates to the in vitro use of at least one lectin chosen from the MAH-II, EEL, PTL-I and GSL-II lectins, for the labeling of cancer stem cells of hormone-dependent cancers, wherein said labeling of cancer stem cells of hormone-dependent cancers is carried out with a lectin conjugated to a fluorophore and is followed by the detection of said cancer stem cells of hormone-dependent cancers by fluorescence microscopy or by fluorescence reader.

In one embodiment, the lectin can be conjugated to a radioisotope.

Thus, according to one embodiment, the present invention relates to the in vitro use of at least one lectin chosen from MAH-II, EEL, PTL-I and GSL-II lectins, for the labeling of cancer stem cells. hormone-dependent, wherein said labeling of cancer stem cells of hormone-dependent cancers is carried out with a lectin conjugated to a radioisotope and is followed by the detection of said labeled cancer stem cells of hormone-dependent cancers by a gamma camera.

In one embodiment, the lectin can be conjugated to an enzyme using a chromogenic substrate or a chemiluminescent substrate.

Thus, according to one embodiment, the present invention relates to the in vitro use of at least one lectin chosen from MAH-II, EEL, PTL-I and GSL-II lectins, for the labeling of cancer stem cells of hormone-dependent cancers, wherein said labeling of cancer stem cells of hormone-dependent cancers is carried out with a lectin conjugated to horseradish peroxidase and is followed by the detection of said labeled cancer stem cells of hormone-dependent cancers by luminescence microscopy or by a luminescence reader by adding a chemiluminescent substrate, such as luminol.

In another embodiment, the present invention relates to the in vitro use of at least one lectin selected from lectins MAH-II, EEL, PTL-I and GSL-II, for the labeling of cancer stem cells of hormone-dependent cancers, in which said labeling of cancer stem cells of hormone-dependent cancers is carried out with a lectin conjugated to horseradish peroxidase and is followed by the detection of said labeled cancer stem cells of hormone-dependent cancers by UV microscopy/visible or by absorbance reader, via the addition of a chromogenic substrate chosen from 3,3-Diaminobenzidine (DAB), 3,3',5,5'-Tetramethylbenzidine (TMB), or 2,2'-azino-bis (3-ethylbenzothiazoline-6-sulphonic acid) (ABTS).

In one embodiment, the lectin can be conjugated to gold beads.

Thus, according to one embodiment, the present invention relates to the in vitro use of at least one lectin chosen from MAH-II, EEL, PTL-I and GSL-II lectins, for the labeling of cancer stem cells of hormone-dependent cancers, wherein said labeling of cancer stem cells of hormone-dependent cancers is carried out with a lectin conjugated to gold beads and is followed by the detection of said labeled cancer stem cells of hormone-dependent cancers by electron microscopy.

In one embodiment, the lectin can be conjugated to biotin, to provide a biotinylated lectin.

Thus, according to one embodiment, the present invention relates to the in vitro use of at least one lectin chosen from MAH-II, EEL, PTL-I and GSL-II lectins, for the labeling of cancer stem cells of hormone-dependent cancers, wherein said labeling of hormone-dependent cancer stem cells is performed with a biotin conjugated lectin and is followed by detection of said cancer stem cells of hormone-dependent cancers labeled with biotin-conjugated lectin by one of the methods described above in which said marker, fluorophore, radioisotope, enzyme, gold beads, is itself conjugated with streptavidin or avidin.

When the labeling of cancer stem cells of hormone-dependent cancers is carried out with a lectin conjugated to biotin and is followed
by the detection of said cancer stem cells of hormone-dependent cancers labeled with the lectin conjugated to biotin, the detection is made:
- by fluorescence microscopy when using of a fluorophore conjugated to streptavidin or avidin,
- by luminescence reader when using an enzyme using a chemiluminescent substrate conjugated to streptavidin or avidin
- by gamma camera when using a radioisotope conjugated to streptavidin or avidin,
- by electron microscopy when using gold beads conjugated to streptavidin or avidin,
- by UV/visible microscopy when using an enzyme using a chromogenic substrate conjugated to streptavidin or avidin.

It was also demonstrated by the inventors that the cancer stem cells of hormone-dependent cancers could be isolated via the use of a lectin chosen from among the lectins MAH-II, EEL, PTL-I and GSL-II, for the labeling of said cancer stem cells of hormone-dependent cancers.

By "isolation of cancer stem cells of hormone-dependent cancers" is meant the extraction of cancer stem cells of hormone-dependent cancers from a biological sample, free of any other cell type.

Thus, the present invention also relates to the use of at least one lectin chosen from MAH-II, EEL, PTL-I and GSL-II lectins, for the labeling of cancer stem cells of hormone-dependent cancers followed by the isolating cancer stem cells from a biological sample, said lectin being conjugated.

This isolation allows enrichment of the sample with cancer stem cells of hormone-dependent cancers. By the term "enrichment" is meant that the proportion of cancer stem cells of hormone-dependent cancers to the total cells contained in the sample is increased, due to the depletion of the sample of non-cancer stem cells.

This is called a sample enriched with cancer stem cells of hormone-dependent cancers.

Thus, by the expression "isolation of cancer stem cells of hormone-dependent cancers" in the context of the invention, is meant "enrichment of the sample with cancer stem cells of hormone-dependent cancers".

Thus, within the meaning of the present invention, the term "isolation" also means the fact of obtaining a population of cells enriched in cancer stem cells of hormone-dependent cancers from a biological sample. For the purposes of the present invention, the term "enriched" denotes a population of cells in which the ratio of number of cancer stem cells/total number of cells is at least 4 as determined by the ratio of Epcam high+cells/Epcam high−cells by flow cytometry.

Enrichment of the sample with cancer stem cells allows more reliable and easier detection and quantification of cancer stem cells since the desired cell population is then present in greater proportion in the sample.

Thus, it has been demonstrated by the Inventors that a biological sample could be enriched in cancer stem cells in a particularly efficient manner by using a lectin chosen from among the lectins MAH-II, EEL, PTL-I and GSL-II.

In a particular embodiment, the isolation of cancer stem cells labeled with at least one lectin selected from MAH-II, EEL, PTL-I and GSL-II lectins can be followed by a cell amplification step. Thus, after isolation of the cells, they can be cultured in a medium that increases the amount of cancer stem cells of hormone-dependent cancers.

In one embodiment, the present invention relates to the in vitro use of at least one lectin selected from MAH-II, EEL, PTL-I and GSL-II lectins, for labeling cancer stem cells of hormone-dependent cancers, wherein said labeling of hormone-dependent cancer stem cells is carried out with a conjugated lectin and is followed by isolation of said labeled hormone-dependent cancer stem cells.

In a particular embodiment, the lectin is conjugated to biotin and the isolation of cancer stem cells of labeled hormone-dependent cancers is carried out via a support functionalized with streptavidin or avidin.

In this embodiment, the cancer stem cells of hormone-dependent cancers labeled with a lectin conjugated to biotin, are fixed on the support functionalized with streptavidin or avidin, by the biotin-streptavidin or biotin-avidin affinity.

The support can also be glass, polydimethylsiloxane (PDMS), silicone, or plastic such as polymethylmethacrylate (PMMA), polystyrene (PS) or cyclic olefin copolymer (COC).

Examples of suitable supports are given in the review by Kim et al. (*Protein immobilization techniques for microfluidics assays*, Kim et al., *Biomicrofluidics*, 7, 041501, 2013). By the term "functionalized" is meant that the support is chemically modified to be coated with streptavidin or immobilized avidin.

The review Kim et al., previously cited, gives examples of support functionalization.

In a more particular embodiment, said support consists of magnetic beads. Thus, according to a particular embodiment of the invention, said support consists of magnetic beads and the isolation of said labeled cancer stem cells of hormone-dependent cancers is carried out by magnetic sorting in the presence of a magnet.

In this embodiment, the cancer stem cells of hormone-dependent cancers with a lectin conjugated to biotin, are attached to the magnetic beads functionalized with streptavidin or avidin, by the biotin-streptavidin or biotin-avidin affinity.

Under the effect of a magnet, cancer stem cells of hormone-dependent cancers attached to the magnetic beads are isolated within the sample. This isolation can be followed by the recovery of the sample enriched with cancer stem cells, by elimination of the supernatant, then by elution of the cancer stem cells bound to said support.

Said elution can be carried out under acidic condition to break the streptavidin-biotin or avidin-biotin bond.

In the particular case where said support consists of magnetic beads and where streptavidin or avidin is linked to the magnetic beads by a DNA bond, said elution is carried out by treatment with DNAse.

According to another embodiment, the lectin used for labeling is a lectin conjugated to a fluorophore and the isolation is carried out by cell sorting in flow cytometry.

Cell sorting by flow cytometry thus makes it possible to obtain a fraction of the sample enriched with cancer stem cells of hormone-dependent cancers.

Flow cytometry is a technique well known to those skilled in the art which makes it possible in particular to sort the cells into different fractions according to their fluorescent labeling.

Cell sorting by flow cytometry in the context of the invention thus makes it possible to obtain:

on the one hand, a fraction of the sample containing cancer stem cells of hormone-dependent cancers labeled with a lectin conjugated to a fluorophore, and on the other hand, a fraction of the sample containing the other cell types contained in the starting sample.

The invention also enables the labeling, isolation and then detection of cancer stem cells of hormone-dependent cancers using at least one conjugated lectin.

In another embodiment, the present invention relates to the in vitro use of at least one lectin selected from the lectins MAH-II, EEL, PTL-I and GSL-II, for the labeling of cancer stem cells of hormone-dependent cancers, wherein said labeling of cancer stem cells of hormone-dependent cancers with a conjugated lectin is followed by isolation of said labeled cancer stem cells of hormone-dependent cancers and then detection of said cancer stem cells of hormone-dependent cancers, via a new labeling of said cancer stem cells of isolated hormone-dependent cancers with a lectin conjugated to a marker chosen from: a fluorophore, a radioisotope, an enzyme, gold beads or biotin.

Thus in another embodiment, the present invention relates to the in vitro use of at least one lectin chosen from MAH-II, EEL, PTL-I and GSL-II lectins, for the labeling of cancer stem cells of hormone-dependent cancers, wherein said labeling of cancer stem cells of hormone-dependent cancers is carried out with a lectin conjugated to a biotin or to a fluorophore and is followed by Isolation of said cancer stem cells of hormone-dependent cancers labeled
via a support functionalized with streptavidin or avidin in the case of a lectin conjugated to biotin as described in the present invention, or
via cytometry in flow in the case of a lectin conjugated with a fluorophore, as described in the present invention, to obtain cancer stem cells of hormone-dependent cancers labeled and isolated,
then a new labeling with a conjugated lectin according to the invention, of said labeled cancer stem cells of hormone-dependent cancers and isolated, followed by the detection of said cells according to the detection methods described in the present application.

Thus, according to one embodiment, the invention relates to the in vitro use, as described above, in which said labeling of cancer stem cells of hormone-dependent cancer target organs is carried out with a conjugated lectin and is monitoring of the detection of said labeled cancer stem cells of hormone-dependent cancers via the detection of the conjugated lectin.

Thus, according to one embodiment, the invention relates to the in vitro use, as described above, in which said labeling of cancer stem cells of hormone-dependent cancer target organs with a lectin conjugated to a marker is monitoring of the isolation of said labeled cancer stem cells of hormone-dependent cancers, in which said marker is biotin and said isolation is carried out via a support functionalized with streptavidin or avidin consisting of magnetic beads and in the presence of a magnet, or wherein said label is a fluorophore and said isolation is carried out by flow cytometry.

According to the invention, said biological sample from which cancer stem cells are isolated or detected is a biological sample of a hormone-dependent cancer target organ such as the breast, uterus, prostate, ovaries, etc. endometrium, thyroid and adrenal glands, taken from a patient with hormone-dependent or non-hormone-dependent cancer or a biopsy taken from a patient suspected of having such cancer.

Thus, according to one embodiment, the invention relates to the in vitro use, as described above, in which said biological sample is a sample of hormone-dependent cancer target organs.

The biological sample can correspond to a solid or liquid biopsy, smear, extemporaneous biopsies as appropriate.

The biological sample of hormone-dependent or non-hormone-dependent cancers can also be a cancer cell line of a hormone-dependent or non-hormone-dependent cancer or a tumor induced in an animal by injection of cancer cell lines, for example in mouse or rat. The cell line is preferably a cancer cell line of hormone-dependent or non-hormone-dependent cancers. According to this embodiment, the induced tumor contains cancer stem cells of hormone-dependent cancers which are advantageously isolated from other cells of the tumor in order to be studied.

According to one embodiment, the present invention relates to the in vitro use of at least one lectin chosen from MAH-II, EEL, PTL-I and GSL-II lectins, for the labeling of cancer stem cells of hormone-dependent, to obtain labeled hormone-dependent cancer stem cells in a biological sample, in which said biological sample consists of cells in suspension. According to another embodiment, the present invention relates to G use in vitro of at least one lectin chosen from MAH-II, EEL, PTL-I and GSL-II lectins, for the labeling of cancer stem cells of hormone-dependent cancers, to obtain labeled hormone-dependent cancer stem cells in a biological sample, wherein said biological sample consists of cell tissue.

The present invention also relates to a method for in vitro labeling of cancer stem cells of hormone-dependent cancers, comprising a step of labeling cancer stem cells of hormone-dependent cancers with at least one lectin chosen from lectins MAH-II, EEL, PTL-I and GSL-II, to obtain labeled cancer stem cells of hormone-dependent cancers, in a biological sample.

This labeling method can be integrated within a method for detecting cancer stem cells of hormone-dependent cancers using a lectin conjugated to a marker chosen from a fluorophore, a radioisotope, an enzyme, biotin or gold beads.

The present invention also relates to an in vitro method of detecting cancer stem cells of hormone-dependent cancers, in a biological sample, comprising:

(a) a step of labeling cancer stem cells of hormone-dependent cancers with at least one lectin chosen from MAH-II, EEL, PTL-I and GSL-II lectins, said lectin being conjugated to a marker chosen from: a fluorophore, a radioisotope, an enzyme, gold beads or biotin, to obtain a biological sample in which the cancer stem cells of hormone-dependent cancers are labeled with at least one lectin,
followed by
(b) a step of detecting said cancer stem cells of hormone-dependent cancers labeled with at least one lectin.

In one embodiment of the method where the lectin is conjugated to a fluorophore, the labeled hormone-dependent cancer stem cells are detected by fluorescence microscopy or fluorescence reader. In one embodiment of the method where the lectin is conjugated to a radioisotope, the labeled cancer stem cells of hormone-dependent cancers are detected by a gamma camera.

In one embodiment of the method where the lectin is conjugated to an enzyme catalyzing the formation of a colored product such as horseradish peroxidase (HRP), alkaline phosphatase, glucose oxidase or β-galactosidase, cancer stem cells marked hormone-dependent cancers are detected by UV/visible microscopy or absorbance reader following the addition of a chromogenic substrate.

In one embodiment of the method where the lectin is conjugated to an enzyme catalyzing the formation of a luminescent product such as HRP, the labeled cancer stem cells of hormone-dependent cancers are detected by luminescence microscopy or by a luminescence reader, following the addition of a chemoluminescent substrate such as luminol.

In one embodiment of the method where the lectin is conjugated to gold beads, the labeled cancer stem cells of hormone-dependent cancers are detected by electron microscopy.

In one embodiment of the method where the lectin is conjugated with biotin, said cancer stem cells of hormone-dependent cancers are detected by one of the detection modes described above in which said marker is conjugated to streptavidin or with avidin. The labeling method can also be integrated within a method of isolating cancer stem cells of hormone-dependent cancers using a conjugated lectin a marker chosen from a fluorophore, a radioisotope, an enzyme, biotin or gold beads.

In one embodiment, the method according to the present invention isolates cancer stem cells of hormone-dependent cancers. This isolation step makes it possible in particular to study cancer stem cells of hormone-dependent cancers detected in a hormone-dependent tumor sample in order, for example, to discover new treatments capable of eliminating these cancer stem cells frequently at the origin of recurrence and metastasis.

By "in vitro isolation method" is meant that the biological sample is enriched with cancer stem cells (CSCs) of hormone-dependent cancers by depleting non-cancer stem cells (CNSCs) from hormone-dependent cancers.

Cancer stem cells of hormone-dependent cancers are specifically separated from other cell types present in the sample, such as possibly non-cancer stem cells of hormone-dependent cancers (CNSCs), by the use of at least one lectin. chosen from MAH-II, EEL, PTL-I and GSL-II lectins.

This enrichment of the sample in CSCs makes it possible to obtain a biological sample in which the cancer stem cells of hormone-dependent cancers are predominantly represented, that is to say they are present in greater quantity compared to other cellular types, in particular compared to CNSCs.

Thus, the present invention also relates to an in vitro method of isolating cancer stem cells of hormone-dependent cancers, in a biological sample comprising:
(a) a step of labeling cancer stem cells of hormone-dependent cancers with at least one lectin chosen from lectins MAH-II, EEL, PTL-I and GSL-II, said lectin being conjugated to biotin or to a fluorophore, to obtain a biological sample in which the cancer stem cells of hormone-dependent cancers are labeled with at least one lectin,
followed by
(b) a step of isolating said cancer stem cells of hormone-dependent cancers labeled with at least one lectin.

In a particular embodiment, the present invention relates to an in vitro method of isolating cancer stem cells of hormone-dependent cancers, in a sample comprising:
(a) a step of labeling cancer stem cells of hormone-dependent cancers with at least one lectin chosen from lectins MAH-II, EEL, PTL-I and GSL-II, said lectin being conjugated to biotin, to obtain a biological sample in which the cancer stem cells of hormone-dependent cancers are labeled with at least one lectin,
followed by
(b) a step of isolating said cancer stem cells of hormone-dependent cancers labeled with at least one lectin, via a support functionalized with streptavidin or avidin.

This isolation can be followed by the recovery of the sample enriched with cancer stem cells, by elimination of the supernatant, then by elution of the cancer stem cells bound to said support.

Said elution can be carried out in an acidic condition to break the streptavidin/avidin-biotin bond.

According to one embodiment, said support consists of magnetic beads functionalized with streptavidin or avidin and said isolation step is carried out by magnetic sorting in the presence of a magnet.

In the particular case where said support consists of magnetic beads and where streptavidin or avidin is linked to the magnetic beads by a DNA bond, said elution is carried out by treatment with DNAse.

In a particular embodiment, the present invention relates to an in vitro method of isolating cancer stem cells of hormone-dependent cancers, in a biological sample comprising:
(a) a step of labeling cancer stem cells of hormone-dependent cancers with at least one lectin chosen from MAH-II, EEL, PTL-I and GSL-II lectins, said lectin being conjugated to a fluorophore to obtain a sample biological in which the cancer stem cells of hormone-dependent cancers are labeled with at least one lectin,
followed by
(b) a step of isolating said cancer stem cells of hormone-dependent cancers labeled with at least one lectin, by cell sorting in flow cytometry. Cell sorting by flow cytometry thus makes it possible to obtain a fraction of the sample enriched in cancer stem cells.

Prior to labeling of the cancer stem cells of hormone-dependent cancers in step (a), the cells in the sample are advantageously dissociated from each other. This dissociation of cells can be carried out according to conventional procedures, for example by using one or more enzymes capable of separating cells from each other without altering the glycans expressed on the surface of the cells, in particular the α 1-2 galactose fucose group. The dissociation of the cells can, for example, be carried out with the Liberase® mixture sold by the company Roche Diagnostic.

The present invention therefore also relates to methods according to the invention, comprising a preliminary step of dissociating the cells of the sample from each other before the labeling step.

Thus, the present invention also relates to an in vitro method of isolating cancer stem cells of target organs of hormone-dependent cancers, in a biological sample comprising:
(a) a step of labeling cancer stem cells of hormone-dependent cancer target organs with at least one lectin chosen from the lectins MAH-II, EEL, PTL-I and GSL-II, said lectin being conjugated to biotin or with a fluorophore, to obtain a biological sample in which the cancer stem cells of hormone-dependent cancer target organs are labeled with at least one lectin,
followed by
(b) a step of isolating said cancer stem cells of hormone-dependent cancer target organs labeled with at least one lectin, said isolation step being carried out via a support functionalized with streptavidin or avidin consisting of magnetic beads and in the presence of a magnet, when said lectin is conjugated with biotin, and said isolation step being carried out by cell sorting in flow cytometry, when said lectin is conjugated to a fluorophore. The study of cancer stem cells for research and diagnostic purposes is now a necessity, in particular to reveal new substances capable of acting against these cells. The study of these cells is also particularly useful in the context of personalized medicine.

Cancer stem cells of hormone-dependent cancers are a particular population of cells which, due to their resistance to chemotherapy treatments, lead to tumor reformation and tumor recurrence. The present invention therefore makes it possible, by detecting or isolating cancer stem cells of hormone-dependent cancers, to assess the risk of recurrence of hormone-dependent or non-hormone-dependent cancer.

The detection of cancer stem cells of hormone-dependent cancers, possibly followed by their quantification, makes it possible to assess the risks of tumor progression.

The present invention therefore also relates to the use of at least one lectin chosen from lectins MAH-II, EEL, PTL-I and GSL-II, for the in vitro diagnosis of the risk of recurrence and/or aggressiveness of a hormone-dependent or non-hormone-dependent cancer to define a prognostic value for the therapeutic adaptation of a hormone-dependent or non-hormone-dependent cancer.

Thus, according to a particular embodiment, the present invention also relates to a method for in vitro diagnosis of the risk of recurrence of hormone-dependent or non-hormone-dependent cancer and/or of the aggressiveness of hormone-dependent or non-hormone-dependent cancer to define a prognostic value for the therapeutic adaptation of a hormone-dependent or non-hormone-dependent cancer, comprising the steps of:

(a) Labeling of cancer stem cells of hormone-dependent cancers of a biological sample with at least one lectin chosen from MAH-II, EEL, PTL-I and GSL-II lectins, to obtain cancer stem cells of hormone cancers-dependent labeled with at least one lectin, in said biological sample, said lectin being conjugated to a marker chosen from a fluorophore, a radioisotope, an enzyme, gold beads or biotin, (b) Detection of said labeled cancer stem cells of hormone-dependent cancers with fluorescence microscopy or fluorescence reader when the lectin is conjugated to a fluorophore or when the lectin is conjugated to biotin and is detected via a fluorophore conjugated to streptavidin or avidin;

luminescence microscopy or luminescence reader when the lectin is conjugated to an enzyme using a chemiluminescent substrate or when the lectin is conjugated to biotin and is detected via an enzyme using a chemiluminescent substrate conjugated to streptavidin or avidin;

gamma camera when the lectin is conjugated to a radioisotope, or when the lectin is conjugated to biotin and is detected via a radioisotope conjugated to streptavidin or avidin;

UV/visible microscopy or absorbance reader when the lectin is conjugated to an enzyme using a chromogenic substrate, or when the lectin is conjugated to biotin and is detected via an enzyme using a chromogenic substrate conjugated to streptavidin or avidin;

electron microscopy when the lectin is conjugated to gold beads, or when the lectin is conjugated to biotin and is detected via gold beads conjugated to streptavidin or avidin;

(c) Optionally quantification of cancer stem cells of hormone-dependent cancers;

(d) Comparison of the intensity of the detection of cancer stem cells of hormone-dependent cancers in said biological sample versus the intensity of the detection of cancer stem cells of hormone-dependent cancers in a healthy sample adjacent to the sample organic, and possibly comparison of the quantification of cancer stem cells of hormone-dependent cancers in said biological sample compared with the quantification of cancer stem cells of hormone-dependent cancers in a healthy sample adjacent to the biological sample (e) Deduction of the risk of recurrence of hormone-dependent or non-hormone-dependent cancer and/or the aggressiveness of hormone-dependent or non-hormone-dependent cancer to define a prognostic value for therapeutic adaptation of hormone-dependent cancer or non-hormone-dependent on the basis of the presence and possibly the quantity of cancer stem cells of hormone-dependent cancers.

According to another particular embodiment, the present invention also relates to a method of in vitro diagnosis of the risk of recurrence of hormone-dependent or non-hormone-dependent cancer and/or of the aggressiveness of hormone-dependent or non-hormone-dependent cancer to define a prognostic value for the therapeutic adaptation of a hormone-dependent or non-hormone-dependent cancer, comprising the steps of:

(a) Labeling of cancer stem cells of hormone-dependent cancers of a biological sample with at least one lectin chosen from MAH-II, EEL, PTL-I and GSL-II lectins, to obtain cancer stem cells of hormone cancers-dependent labeled with at least one lectin in said biological sample, said lectin being conjugated to a marker chosen from a fluorophore or biotin, (b) Isolation of cancer stem cells of hormone-dependent cancers labeled with at least one conjugated lectin:

when labeling with a lectin conjugated to biotin, said isolation is carried out via a support functionalized with streptavidin or avidin, in particular said functionalized support consists of magnetic beads functionalized with streptavidin or avidin and said isolation is carried out by magnetic cell sorting in the presence of a magnet, or when labeling with a lectin conjugated to a fluorophore, said isolation is carried out by cell sorting in flow cytometry.

(c) New labeling of cancer stem cells of hormone-dependent cancers isolated with at least one lectin chosen from lectins MAH-II, EEL, PTL-I and GSL-II, to obtain cancer stem cells of hormone-dependent cancers isolated and marked with the new marking, said lectin being conjugated to a marker chosen from a fluorophore, a radioisotope, an enzyme, gold beads or biotin, (d) Detection of said cancer stem cells of hormone-dependent cancers isolated and labeled by the new labeling by fluorescence microscopy or fluorescence reader when the lectin is conjugated to a fluorophore or when the lectin is conjugated to biotin and is detected via a fluorophore conjugated to streptavidin or avidin;

luminescence microscopy or luminescence reader when the lectin is conjugated to an enzyme using a chemiluminescent substrate or when the lectin is conjugated to biotin and is detected via an enzyme using a chemiluminescent substrate conjugated to streptavidin or avidin;

gamma camera when the lectin is conjugated to a radioisotope, or when the lectin is conjugated to biotin and is detected via a radioisotope conjugated to streptavidin or avidin;

UV/visible microscopy or absorbance reader when the lectin is conjugated to an enzyme using a chromogenic substrate, or when the lectin is conjugated to biotin and is detected via an enzyme using a chromogenic substrate conjugated to streptavidin or avidin;

electron microscopy when the lectin is conjugated to gold beads, or when the lectin is conjugated to biotin and is detected via gold beads conjugated to streptavidin or avidin;

(e) Optionally quantification of cancer stem cells of hormone-dependent cancers;

(f) Comparison of the intensity of the detection of cancer stem cells of hormone-dependent cancers in said biological sample versus the intensity of the detection of cancer stem cells of hormone-dependent cancers in a healthy sample adjacent to the sample organic, and optionally comparing the quantification of cancer stem cells of hormone-dependent cancers in said biological sample versus the quantification of cancer stem cells of hormone-dependent cancers in a healthy sample adjacent to the biological sample;

(g) Deduction of the risk of recurrence of hormone-dependent or non-hormone-dependent cancer and/or the aggressiveness of hormone-dependent or non-hormone-dependent cancer to define a prognostic value for therapeutic adaptation of hormone-dependent or non-hormone-dependent cancer on the basis of the presence and possibly the quantity of cancer stem cells of hormone-dependent cancers. The intensity of the detection of cancer stem cells of hormone-dependent cancers, and possibly their quantification, is compared against a healthy sample adjacent to the biological sample.

The healthy sample adjacent to the biological sample is used as a control.

The term "healthy sample adjacent to the biological sample" means a sample taken from the same individual as the biological sample, but in a tissue close to that from which said biological sample is taken, and which does not present tumor cells on anatomo-pathology analysis and which does not present cancer stem cells by the method according to the invention.

The healthy sample is therefore a sample characterized by the absence of tumor cells by analysis by pathology and the absence of cancer stem cells by the method according to the invention.

The quantification of cancer stem cells of hormone-dependent cancers makes it possible to determine the aggressiveness of hormone-dependent or non-hormone-dependent cancer.

This quantification can be established by different methods such as: flow cytometry, western blot, quantitative PCR with generic markers such as Oct-4, cMyc1, Gli-1 or EpCam or a clonogenicity test.

Several of these methods can also be used in parallel in order to form a beam of presence of CSCs and thus increase the reliability of the quantification.

In a particular embodiment, the quantification of cancer stem cells of hormone-dependent cancers is carried out by a clonogenicity test.

A clonogenicity test involves culturing the biological sample to observe the ability of cells to reform tumor spheres. This property of self-renewal and self-replication is specific to cancer stem cells; a single cancer stem cell is thus at the origin of a tumor sphere formed. Thus, counting the tumor spheres formed makes it possible to quantify the cancer stem cells in the sample.

These methods, advantageously qPCR with generic markers such as Oct-4, c-Myc, Gli-1 or EpCam and the clonogenicity test, also allow the detection of cancer stem cells in order to determine the presence or absence of these. cells after the cancer stem cell isolation step. These methods are therefore presented as alternatives to the aforesaid steps (c) and (d), corresponding respectively to the new labeling and to the detection of cancer stem cells of isolated hormone-dependent cancers.

This detection is facilitated and made more reliable by the enrichment of the sample with cancer stem cells.

Detection by these methods also makes it possible to validate the efficiency of the enrichment of the sample with cancer stem cells of hormone-dependent cancers by the method according to the invention, i.e. the efficiency of the method in isolating cancer stem cells of hormone-dependent cancers.

In the diagnostic methods of the present invention, the higher the intensity of detection in the biological sample compared to a healthy sample adjacent to the biological sample, the greater the risk of recurrence of the hormone-dependent or non-hormone-dependent cancer is strong and the more aggressive the cancer.

Likewise, the higher the quantity of cancer stem cells of hormone-dependent cancers in the biological sample compared to a healthy sample adjacent to the biological sample, the greater the risk of recurrence of the hormone-dependent or non-hormone-dependent cancer is strong and the more aggressive the cancer.

The detection and quantification of cancer stem cells of hormone-dependent cancers in a biological sample thus make it possible to determine the aggressiveness of the hormone-dependent or non-hormone-dependent cancer and its capacity to develop.

The detection and quantification of cancer stem cells of hormone-dependent cancers are also part of a personalized medicine approach. Indeed, the detection of cancer stem cells of hormone-dependent cancers in the biological sample, allowing the prognostic value of the treatment to be assessed, thus makes it possible to adapt the treatment.

All of the detection and isolation methods and all of the diagnostic methods described above and comprising the use of at least one lectin chosen from MAH-II, PTL-I, GSL-II and EEL lectins, can also be produced with at least two lectins or at least three lectins chosen from the lectins MAH-II, PTL-I, GSL-II and EEL, or even with the four lectins MAH-II, PTL-I, GSL-II and EEL. Thus, the various mixtures of lectins described in the present application, as well as the various ratios of lectin in these mixtures, are applicable to the performance of all the detection and isolation methods and all of the diagnostic methods described in the present application.

The present invention also relates to a kit for the in vitro detection of cancer stem cells of hormone-dependent cancers, in a biological sample, comprising at least one lectin chosen from lectins MAH-II, EEL, PTL-I and GSL-II, said lectins being conjugated to a marker chosen from: a fluorophore, a radioisotope, an enzyme, gold beads or biotin.

The present invention also relates to a kit for the in vitro isolation of cancer stem cells of hormone-dependent cancers, in a biological sample, comprising at least one lectin chosen from lectins MAH-II, EEL, PTL-I and GSL-II, said lectin being conjugated to biotin, and magnetic beads functionalized with streptavidin.

The present invention also relates to a kit for the in vitro isolation of cancer stem cells of hormone-dependent cancers, in a biological sample comprising at least one lectin chosen from lectins MAH-II, EEL, PTL-I and GSL-II, said lectin being conjugated to a fluorophore.

The present invention also relates to an in vitro diagnostic kit of the risk of recurrence of hormone-dependent or non-hormone-dependent cancer and/or the aggressiveness of hormone-dependent or non-hormone-dependent cancer to define a prognostic value for the therapeutic adaptation of a hormone-dependent or non-hormone-dependent cancer comprising:
- at least one lectin chosen from MAH-II, EEL, PTL-I and GSL-II lectins, said lectin being conjugated to biotin, and magnetic beads functionalized with streptavidin, and optionally at least one lectin chosen from MAH-II, EEL, PTL-I and GSL-II lectins, conjugated to a fluorophore, a radioisotope, an enzyme or gold beads. The present invention also relates to an in vitro diagnostic kit of the risk of recurrence of hormone-dependent or non-hormone-dependent cancer and/or the aggressiveness of hormone-dependent or non-hormone-dependent cancer to define a prognostic value for the. therapeutic adaptation of hormone-dependent or non-hormone-dependent cancer, comprising:
- at least one lectin chosen from MAH-II, EEL, PTL-I and GSL-II lectins, said lectin being conjugated to a fluorophore,
- and optionally at least one lectin chosen from MAH-II, EEL, PTL-I and GSL-II lectins, conjugated to biotin, a radioisotope, an enzyme or gold beads.

The present invention also relates to an in vitro diagnostic kit of the risk of recurrence of hormone-dependent or non-hormone-dependent cancers and/or of the aggressiveness of hormone-dependent or non-hormone-dependent cancers to define a prognostic value for the therapeutic adaptation of hormone-dependent or non-hormone-dependent cancers, comprising at least one lectin chosen from lectins MAH-II, EEL, PTL-I and GSL-II, said lectin being conjugated to biotin, and magnetic beads functionalized with streptavidin, and optionally at least one lectin chosen from MAH-II, EEL, PTL-I and GSL-II lectins, conjugated to a fluorophore, a radioisotope, an enzyme or gold beads, or comprising at least one lectin chosen from lectins MAH-II, EEL, PTL-I and GSL-II, said lectin being conjugated to a fluorophore, and optionally at least one lectin chosen from lectins MAH-II, EEL, PTL-I and GSL-II, conjugated to biotin, a radioisotope, an enzyme or gold beads.

The kits according to the present invention described above can comprise at least two conjugated lectins chosen from MAH-II, EEL, PTL-I and GSL-II lectins, said at least two conjugated lectins being in equal quantity.

The kits according to the present invention described above can comprise at least two conjugated lectins chosen from MAH-II, EEL, PTL-I and GSL-II lectins, said at least two conjugated lectins being in unequal quantity.

Thus, in one embodiment, the kits according to the present invention can comprise two conjugated lectins chosen from: (MAH-II, EEL), (EEL, MAH-II), (MAH-II, PTL-I), (PTL-I, MAH-II), (MAH-II, GSL-II), (GSL-II, MAH-II), (EEL, PTL-I), (PTL-I, EEL), (GSL-II, EEL), (EEL, GSL-II), (PTL-I, GSL-II), (GSL-II, PTL-I), said at least two lectins being in unequal quantity in said kits, in particular in a ratio by weight of 2:1.

The kits according to the present invention described above can comprise at least three conjugated lectins chosen from MAH-II, EEL, PTL-I and GSL-II lectins, said at least three conjugated lectins being in equal quantity.

The kits according to the present invention described above may comprise at least three conjugated lectins chosen from among the MAH-II, EEL, PTL-I and GSL-II lectins, said at least three conjugated lectins being in unequal quantity.

Thus, according to a particular embodiment, the kits according to the present invention can comprise three conjugated lectins chosen from: (MAH-II, EEL, PTL-I), (EEL, MAH-II, PTL-I), (PTL-I, MAH-II, EEL), (MAH-II, EEL, GSL-II), (EEL, MAH-II, GSL-II), (GSL-II, MAH-II, EEL), (EEL, GSL-II, PTL-I), (PTL-I, EEL, GSL-II), (GSL-II, EEL, PTL-I), said three lectins being in unequal quantity in said kits, in particular in a ratio by weight of 2:1:1.

The kits according to the present invention described above can comprise four conjugated lectins chosen from MAH-II, EEL, PTL-I and GSL-II lectins, said four conjugated lectins being in equal quantity.

The kits according to the present invention described above can comprise four conjugated lectins chosen from MAH-II, EEL, PTL-I and GSL-II lectins, said four conjugated lectins being in unequal quantity.

Thus, according to a particular embodiment, the kits according to the present invention can comprise four conjugated lectins chosen from: (MAH-II, EEL, PTL-I, GSL-II), (MAH-II, EEL, GSL-II, PTL-I), (MAH-II, PTL-I, EEL, GSL-II), (MAH-II, PTL-I, GSL-II, EEL), (MAH-II, GSL-II, PTL-I, EEL), (MAH-II, GSL-II, EEL, PTL-I), (EEL, MAH-II, PTL-I, GSL-II), (EEL, MAH-II, GSL-II, PTL-I), (EEL, PTL-I, MAH-II, GSL-II), (EEL, PTL-I, GSL-II, MAH-II), (EEL, GSL-II, MAH-II, PTL-I), (EEL, GSL-II, PTL-I, MAH-II), (GSL-II, EEL, PTL-I, MAH-II), (GSL-II, EEL, MAH-II, PTL-I), (GSL-II, PTL-I, EEL, MAH-II), (GSL-II, PTL-I, MAH-II, EEL), (GSL-II, MAH-II, EEL, PTL-I), (GSL-II, MAH-II, PTL-I, EEL), (PTL-I, GSL-II, MAH-II, EEL), (PTL-I, GSL-II, EEL, MAH-II), (PTL-I, EEL, MAH-II, GSL-II), (PTL-I, EEL, GSL-II, MAH-II), (PTL-I, MAH-II, EEL, GSL-II), (PTL-I, MAH-II, GSL-II, EEL), said four lectins being in unequal amount in said kits, in particular in a weight ratio of 2:1:1:1.

According to another embodiment, the invention also relates to in vitro diagnostic kits of the risk of recurrence of hormone-dependent or non-hormone-dependent cancers and/or the aggressiveness of hormone-dependent or non-hormone-dependent cancers to define a prognostic value for the therapeutic adaptation of hormone-dependent or non-hormone-dependent cancers,
include the mixture of MAH-II and EEL lectins, and/or the mixture of MAH-II and PTL-I lectins, and/or the mixture of MAH-II and GSL-II lectins, and/or the mixture of EEL and PTL-I lectins, and/or the mixture of EEL and GSL-II lectins, and/or the mixture of PTL-I and GSL-II lectins, and/or the mixture of MAH-II, EEL and PTL-I, and/or the mixture of MAH-II, EEL and GSL-II lectins, and/or the mixture of MAH-II, PTL-I and GSL-II lectins and/or the mixture of EEL, PTL-I and GSL-II lectins and/or the mixture of MAH-II, EEL, PTL-I and GSL-II lectins, said lectins being conjugated to biotin, and magnetic beads functionalized with streptavidin, and optionally the mixture of MAH- II and EEL lectins, and/or the mixture of MAH-II and PTL-I lectins, and/or the mixture of MAH-II and GSL-II lectins, and/or the mixture of EEL and PTL-I lectins, and/or the mixture of EEL and GSL-II lectins, and/or the mixture of lectins PTL-I and GSL-II, and/or the mixture of MAH-II, EEL and PTL-I, and/or the mixture of lectins MAH-II, EEL and GSL-II, and/or the mixture of MAH-II, PTL-I and GSL-II lectins and/or the mixture of EEL, PTL-I and GSL-II lectins and/or the mixture of MAH-II, EEL, PTL-I and GSL-II lectins, said lectins being conjugated to a fluorophore, a radioisotope, an enzyme or gold beads, or include the mixture of MAH-II and EEL lectins, and/or the mixture of MAH-II and PTL-I lectins, and/or the mixture of MAH-II and GSL-II lectins, and/or the mixture of EEL and lectins PTL-I, and/or the mixture of EEL and GSL-II lectins, and/or the mixture of PTL-I and GSL-II lectins, and/or the mixture of MAH-II, EEL and PTL-I, and/or the mixture of MAH-II, EEL and GSL-II lectins, and/or the mixture of MAH-II, PTL-I and GSL-II lectins and/or the mixture of EEL, PTL-I and GSL-II lectins and/or the mixture of MAH-II, EEL, PTL-I and GSL-II lectins, said lectins being conjugated to a fluorophore, and optionally the mixture of MAH-II and EEL lectins, and/or the mixture of MAH-II and PTL-I lectins, and/or the mixture of MAH-II and GSL-II lectins, and/or the mixture of EEL and PTL-I lectins, and/or the mixture of EEL and GSL-II lectins, and/or the mixture of lectins PTL-I and GSL-II, and/or the mixture of MAH-II, EEL and PTL-I, and/or the mixture of MAH-II, EEL and GSL-II lectins, and/or the mixture of MAH-II, PTL-I and GSL-II lectins and/or the mixture of lectins EEL, PTL-I and GSL-II and/or the mixture of lectins MAH-II, EEL, PTL-I and GSL-II, said lectins being conjugated to biotin, a radioisotope, an enzyme or gold beads.

Cancer stem cells are examined from a sorting of cells from the MCF-7 line, using the Epcam High+/Epcam High– ratio, with the use of magnetic beads onto which streptavidin is grafted and the use of the following biotinylated lectins: Biotinylated MAH-II (Lectin MAH-II), Biotinylated EEL (Lectin EEL), Biotinylated PTL-I (Lectin PTL-I), Biotinylated GSL-II (Lectin GSL-II), a mixture in equal quantity (weight ratio 1:1) of biotinylated lectins MAH-II/EEL (Mixture 1) or mixture in unequal quantity (weight ratio 2:1) of biotinylated lectins MAH-II/EEL (Mixture 2).

Figure 2:
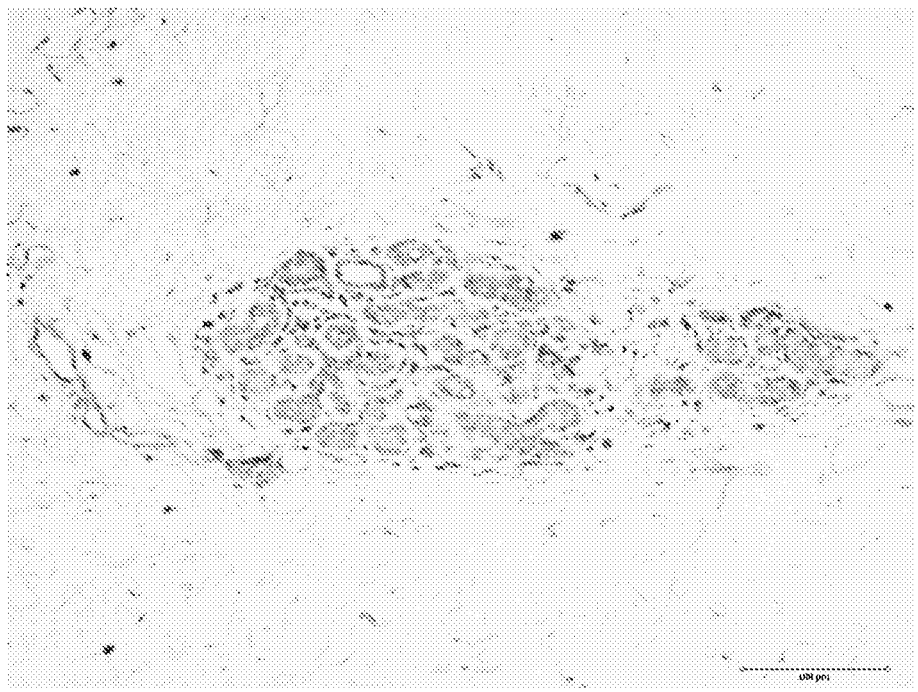
Figure 2:
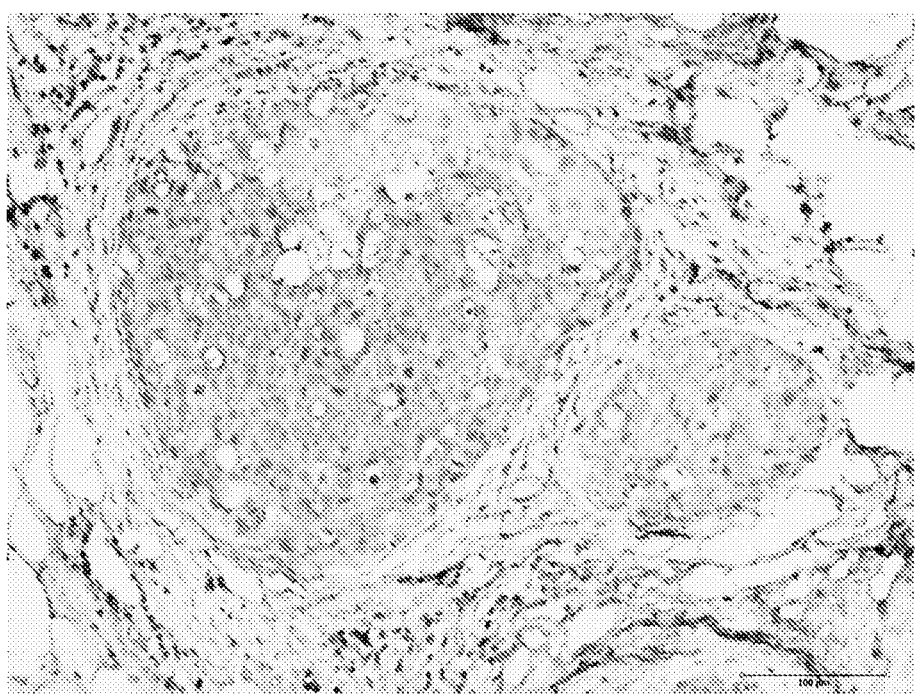

FIG. 2 shows sections of breast tissue samples taken from biopsies of healthy (FIG. 2A) or breast cancer (FIG. 2B) patients:

FIG. 2A: Treatment of healthy tissue by mixing an equal quantity of the two MAH-II/EEL lectins (1:1 ratio) demonstrates the absence of labeling of the cells, demonstrating the absence of breast cancer stem cells in healthy tissue.

FIG. 2B: Treatment of tumor tissue by mixing an equal amount of the two MAH-II/EEL lectins (1:1 ratio) demonstrates the ability of this mixture of lectins to selectively label cancer stem cells of hormone-dependent cancer target organs, in this case to selectively label breast cancer stem cells (dark area).

Figure 3:
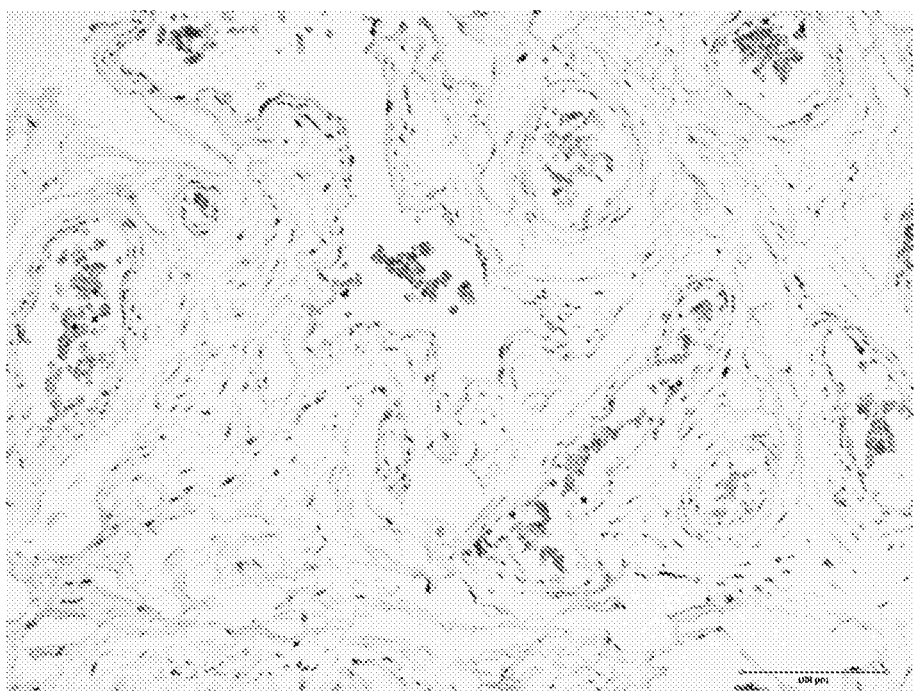
Figure 3:
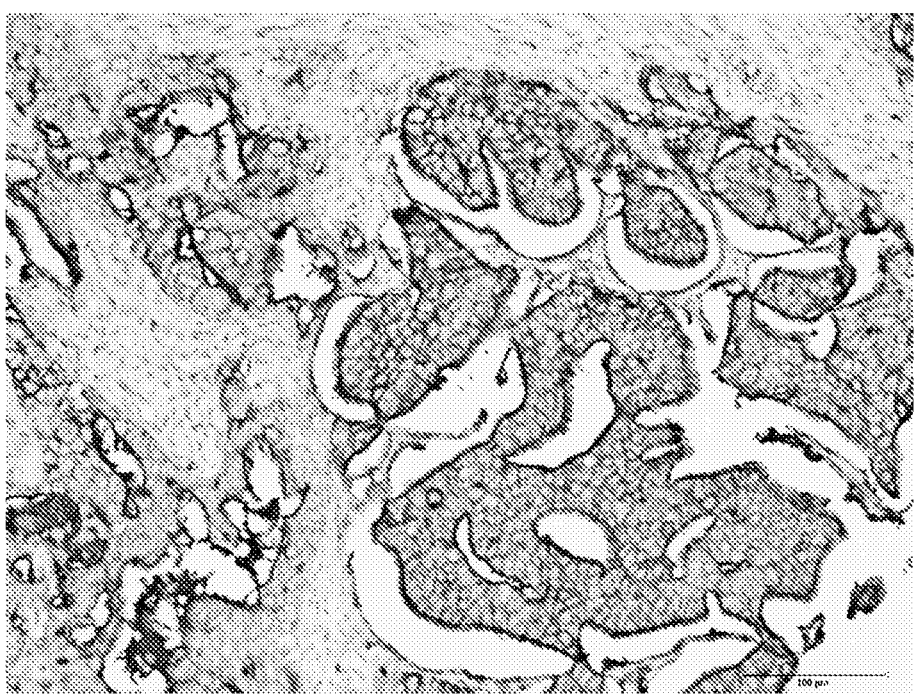

FIG. 3 shows sections of ovarian tissue samples taken from biopsies of healthy (FIG. 3A) or ovarian cancer (FIG. 3B) patients:

FIG. 3A: Treatment of healthy tissue by mixing an equal amount of the two MAH-II/EEL lectins (1:1 ratio) demonstrates the absence of labeling of the cells, demonstrating the absence of ovarian cancer stem cells in healthy tissue.

FIG. 3B: Treatment of tumor tissue by mixing an equal amount of the two MAH-II/EEL lectins (1:1 ratio) demonstrates the ability of this mixture of lectins to selectively label cancer stem cells of hormone-dependent cancer target organs, in this case to selectively mark ovarian cancer stem cells (dark area).

Figure 4:
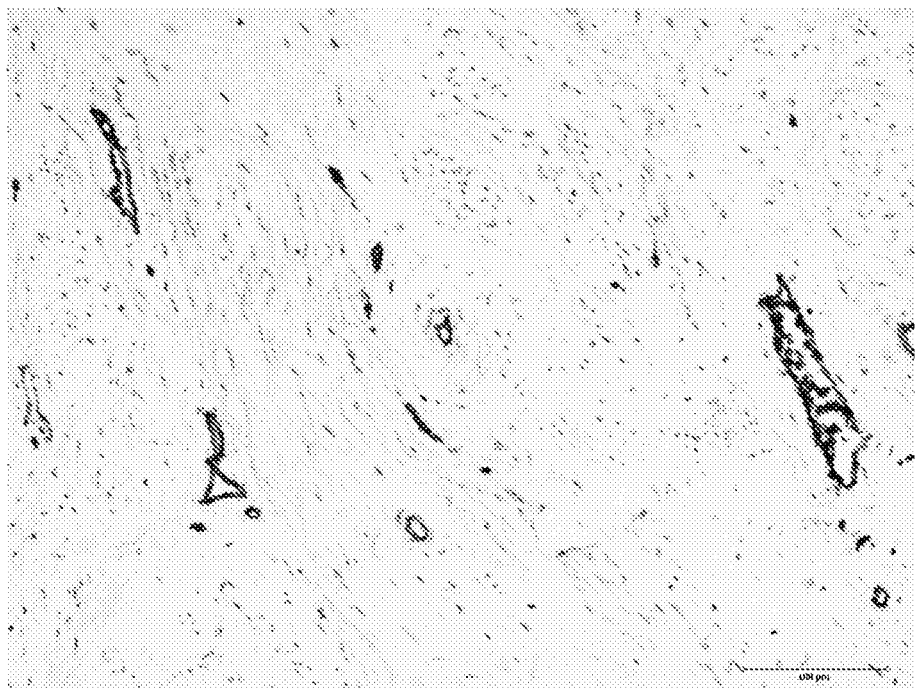
Figure 4:
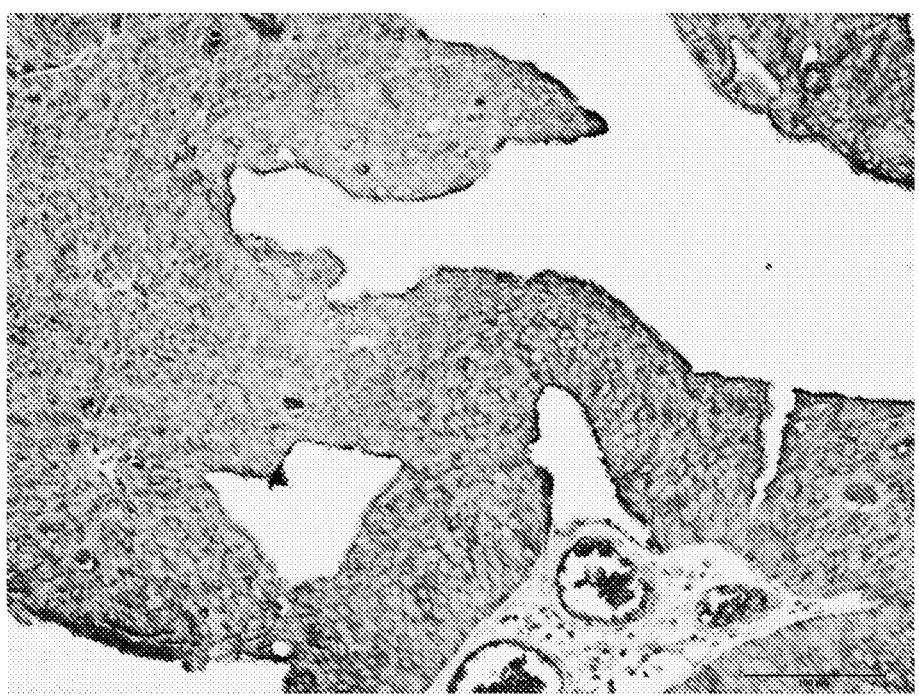

FIG. 4 shows sections of uterine tissue samples taken from biopsies of healthy (FIG. 4A) or uterine cancer (FIG. 4B) patients:

FIG. 4A: Treatment of healthy tissue by mixing an equal amount of the two MAH-II/EEL lectins (1:1 ratio) demonstrates the absence of cell labeling, demonstrating the absence of uterine cancer stem cells in healthy tissue.

FIG. 4B: Treatment of tumor tissue by mixing an equal amount of the two MAH-II/EEL lectins (1:1 ratio) demonstrates the ability of this mixture of lectins to selectively label cancer stem cells of hormone-dependent cancer target organs, in this case to selectively mark cancer stem cells in the uterus (dark area).

DESCRIPTION OF THE PREFERRED EMBODIMENTS

Example 1: Protocol for the Isolation of Cancer Stem Cells from Breast Cancer

I. Materials Required

Reagents and Materials
  Biotinylated individual lectin or mixture of biotinylated lectins specifically marking Cancer Stem Cells of hormone-dependent cancers, here breast cancer (prepared from individual lectins from Vector Laboratories and Emelca Biosciences)
  CELLection Biotin Binder kit (Invitrogen) containing magnetic beads coupled to streptavidin by a DNA bond
  Magnet
Buffers
  Versene (Invitrogen) comprising phosphate buffered saline (PBS) and EDTA
  Buffer 1: PBS (Phosphate buffered saline without $Ca^{2+}$ and $Mg^{2+}$) with 0.1% BSA (Bovine serum albumin), pH 7.4
  Buffer 2: PBS (Phosphate Buffer Saline without $Ca^{2+}$ and $Mg^{2+}$) with 0.1% BSA (Bovine Serum Albumin) and 0.6% sodium citrate
  Buffer 3: RPMI 1640 with 1% FCS (fetal calf serum), 1 mM $CaCl_2$ and 5 mM $MgCl_2$, pH 7.0-7.4.

II. Duration of the Experiment 20 min to prepare cells
20 min to label cells
20 min to incubate labeled cells with the beads
10 min to recover the suspension not enriched in CSCs
15 min to break the CSCs/beads bond
5 min to recover the suspension enriched in CSCs of interest
TOTAL: 1h30

III. Magnetic Sorting Procedure:

1. Preparation of cells. The cells of the MCF-7 line (mammary cancer cell line) are detached from their support with Versene for 10 min at 37° C.

2. The cells are counted and the number of cells is adjusted to $1.10^7$ in the sample.
3. The cell suspension is centrifuged at 300 g for 10 min then the supernatant is eliminated.
4. Blocking of non-specific sites. 1 mL of Buffer 2 is added.
5. Cell labeling. A total amount of lectins of 10 µg is added, so that when there is a plurality of lectins, the amounts of each are the same.

Thus, are added:
10 pg of an individual biotinylated lectin chosen from: chosen from MAH lectins
II, EEL, PTL-I and GSL-II, or
5 pg of each lectin for mix 1 (MAH-II/GSL-II)
6.66 pg of MAH-II lectin and 3.33 pg of GSL-II lectin for mixture 2.

The mixture then obtained is incubated for 10 min at 4° C.

6. 500 pL of Buffer 2 is added in order to wash the cells and the suspension is centrifuged at 300 g for 10 min and the supernatant is removed.
7. Addition of beads. The cells are resuspended in 1 mL of Buffer 2 and then 25 µL of magnetic beads coupled to streptavidin washed beforehand are added and resuspended using Buffer 1. The mixture is incubated for 20 min at 4° C. with gentle stirring.
8. Recovery of the suspension NOT enriched in CSCs. The tube is then placed on the magnet for 2 min. Cells labeled with biotinylated lectins and bound to magnetic beads coupled to streptavidin, precipitate in the direction of the magnet (magnetic cell sorting) and are then separated from unlabeled cells. The supernatant containing unlabeled cells is then removed, keeping the tube placed on the magnet, and stored in a Falcon tube.
9. The tube containing the labeled cancer stem cells is then removed from the magnet. 1 mL of Buffer 1 is added. The tube is vortexed and replaced on the magnet for 2 min, then the supernatant is again removed and stored in the same falcon as in step 8. This step is repeated twice.
10. The labeled cancer stem cells, still bound to the magnetic beads, are resuspended using 200 ml of Buffer 3 preheated to 37° C. 4 µl of cell/bead binding cleavage buffer consisting of DNaseI are added. This mixture is incubated for 15 min at room temperature with gentle stirring.
11. The suspension is stirred with a pipette vigorously 5 to 10 times in order to facilitate the release of the cells.
12. Recovery of the suspension enriched in CSCs. The tube is placed on the magnet for 2 min. The magnetic beads are then separated from the labeled cancer stem cells and the supernatant containing the labeled cancer stem cells is transferred to a tube containing 200 µL of buffer 3 preheated to 37° C. Steps 11 and 12 can be repeated again to enrich the yield.

These experiments were performed under similar conditions with each of the lectins individually (MAH-II, EEL, PTL-I, GSL-II), a mixture in equal quantity (weight ratio 1:1) of two lectins (Mixture 1: MAH-II/EEL) or a mixture in unequal quantity (weight ratio 2:1) of two lectins (Mixture 2:2 MAH-II/EEL).

Figure 1:
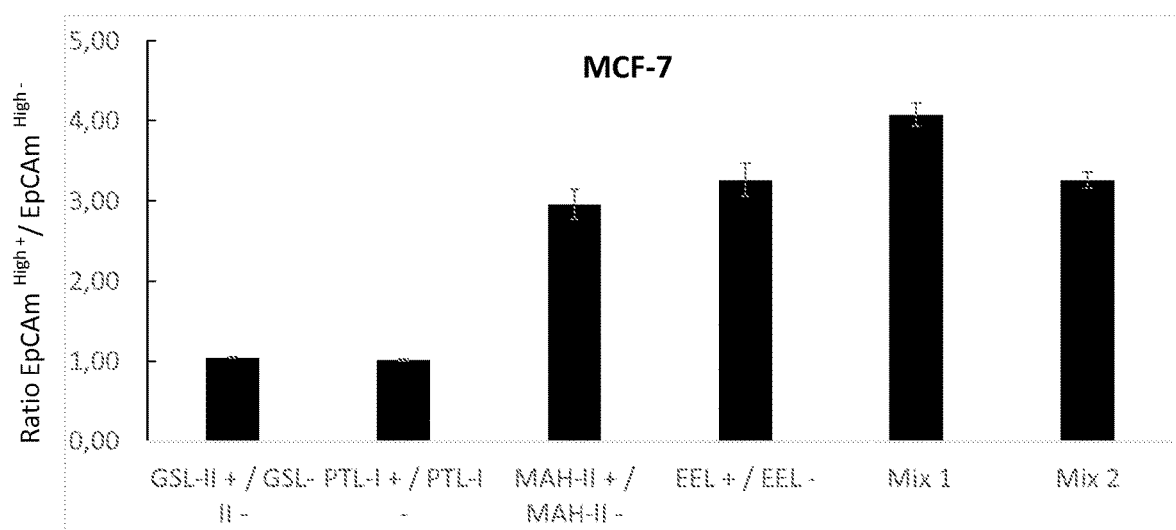
FIG. 1 shows the results of the separation of cancer stem cells of hormone-dependent cancers on a sample of cells from the MCF-7 line, a line of cancer cells of breast origin.

The results of these different tests are presented in FIG. 1.

As shown by the results of these tests, the use of mixture 1, namely MAH-II lectins and EEL in an equimolar mixture, allows the isolation of cancer stem cells of hormone-dependent cancer target organs, in this case breast cancer, and this predominantly compared to other trials carried out in parallel.

These results also make it possible to demonstrate that the cancer stem cells of breast cancer present on their surface predominantly O-linked glycans and in particular the disialyl-T group [NeuAc α2-3Gal α1-3 (NeuAc α2-6) GalNAc] and galactosylated glycans, in particular the Fucα1-2Gal β1-3GlcNAc group of the H antigen.

Indeed, MAH-II and EEL lectins reveal a particular efficiency in isolating and detecting this type of cancer stem cells.

Example 2: Clonogenicity Test

The objective of a clonogenicity test is to observe the capacity of cells to reform spheres (corresponding in the patient to the reform of a tumor mass) and therefore their proliferative capacity.

The clonogenicity test is in this example used to confirm the presence of cancer stem cells of hormone-dependent cancers and to quantify said cells in a sample after isolation of cancer stem cells of hormone-dependent cancers by the isolation method described herein. invention. It thus makes it possible to demonstrate the effectiveness of the isolation method according to the invention compared to a control sample not subjected to this method (unsorted cells).

The clonogenicity tests were carried out in a 6-well plate at a density of 500 cells/cm$^2$ in a medium of RPMI composition (Gibco) supplemented with 50 units/ml of penicillin, 50 units/ml of streptomycin (Gibco) and 2.4 g/L of sodium bicarbonate, 1 M of HEPES buffer (Sigma Aldrich, Saint-Quentin-Fallavier, France), 1× progesterone (Sigma Aldrich), 1× putrescine (Sigma), 0.025 g/ml heparin (Sigma Aldrich), 30% (m/v) glucose (Sigma Aldrich), 1× Growth Supplement B27 (Invitrogen, Carlsbad, CA), 20 ng/mL EGL (Sigma Aldrich), 20 ng/mL Human Basic LGL (Sigma Aldrich), 1× insulin-transferrin-sodium selenite supplement (Roche diagnostics, Meylan, France).

The evolution of colonies was observed after incubation at 37° C. in a CO$_2$ atmosphere for three weeks and quantified with ImageJ® software.

Cancer stem cells of hormone-dependent cancer target organs isolated using the isolation method described in the present invention lead to the formation of spheres unlike the control. This is a clonogenicity test having unsorted cells as control (T-), against cells sorted positively by biotinylated MAH-II (MAH-II Lectin), biotinylated EEL (Lectin EEL), biotinylated PTL-I (Lectin PTL-I), biotinylated GSL-II (Lectin GSL-II), mixing in equal quantity (weight ratio 1:1) of biotinylated lectins MAH-II/EEL (Mixture 1), mixing in unequal quantity (2:1 weight ratio) of biotinylated lectins 2 MAH-II/EEL (Mixture 2). The method according to the present invention therefore makes it possible to obtain stem cells capable of reforming tumors (results not shown).

Example 3: Visible Labeling of Lectins on a Paraffinized Histological Section (FIG. 2: Breast)

Equipment used: Paraffin blocks, Ice, Microtome, Superfrost® slides, Bond Max automaton (Leica Microsystems) with computer, Leica consumables (alcohol, washing buffer, ER1 buffer, dewax buffer, labels, coverslips, tubes), PBS-buffer 5% BSA, Biotinylated Lectins (MAH-II and GSL-II (Vector Lab), EEL and PTL-I (Emelca Biosciences)), Bond Intense R detection kit (Leica), Leica mounting medium, coverslips and microscope.

The paraffin blocks containing the breast cancer samples from each of the patients identified by their number (given by the pathological anatomy department) were placed in ice for about 1 hour in order to be cooled, in order to facilitate their microtome cut to a thickness of 4 μm.

So-called "superfrost" blades, this for maximum adhesion of the cut tissue have been identified by the same numbers as those on the blocks. A drop of water was placed in the center of each of these slides.

The sections were made with a microtome and placed on the drop of water previously deposited. The slides were then placed on a hotplate at 37° C. to facilitate their adhesion and the excess water was removed. All of the slides produced were placed in an oven at 37° C. in order to dry them.

The rest of the manipulation involved the Bond Max automaton from Leica connected to a computer with software controlling the automaton. While the slides are in the oven, all of the immunohistochemical labeling manipulation was prepared, starting by checking the level on the automatic device of each of the products necessary for carrying out the manipulation, then identification of the blades with their same number on the software controlling the PLC. Labels allowing a standardized protocol were generated. The dilution of lectins and their quantity were calculated and the necessary kit prepared. It should be noted that each of the products used had to be scanned and the level reset to zero before each of the experiments carried out.

The labels were then stuck on their corresponding blades at the outlet of the oven and the coverslips, plastic elements placed on the cup allowing a homogeneous distribution of the product over the entire surface of the blade during handling thanks to the contact properties, were placed on each of the slides.

The slide rack was placed in the machine and after recognition by the reader of each of the elements and slides identified by their bar codes present on the labels, manipulation was initiated. It began with heat dewaxing using the Dewax product from Leica, which subsequently made the antibodies accessible. This step as well as all the others was followed by washes, thanks to the 10× Bond Wash previously diluted, this on three occasions.

This step was followed by a pretreatment for 5 min with ER1 buffer from Leica, corresponding to a citrate buffer at pH=6, which makes it possible to unmask the antigens, that is to say to make them accessible.

Biotinylated lectin or a mixture of two biotinylated lectins chosen from MAH-II, EEL, PTL-I and GSL-II, diluted in a solution of PBS with 5% BSA (in order to prevent non-specific attachments due to its saturating power), was placed on the cup for 20 min. The Bond Intense R detection kit (Leica) thanks to the intervention of a streptavidin-HRP playing the role of secondary antibody made it possible, through its properties, to reveal the biotinylated lectin (s) in brown thanks to the properties of DAB, a substrate HRP (horseradish peroxidase) enzyme, which reveals the biotin/streptavidin-HRP complex. A step of bluish counterstaining thanks to the presence of hematoxylin was then carried out for 7 min in order to make the entire sample identifiable.

The slides have been removed from the machine. The sections were then rehydrated by dipping the slides manually in an alcohol bath twice for 5 min. This rehydration step was continued with a toluene bath for 5 min as well. The slides could therefore be mounted by adding a drop of mounting medium (Leica).

The slides were finally observed under a microscope.

The labeling of healthy tissue, obtained from a breast biopsy, by mixing an equal amount of the two MAH-II/EEL lectins (ratio 1:1) showed the absence of labeling of the cells. It can therefore be deduced from this that there are no breast cancer stem cells in this tissue (FIG. 2A).

Several cell types coexist in tumor tissue: non-tumor stem cells, non-tumor stem cells, tumor stem cells and non-tumor non-stem cells. The labeling of a tumor tissue by the mixture in equal quantity of MAH-II/EEL lectins (ratio 1:1) demonstrates the ability of this mixture of lectins to selectively label cancer stem cells of hormone-dependent cancer target organs, in this case to selectively label breast cancer stem cells (FIG. 2B).

Example 4: Visible Labeling of Lectins on a Paraffinized Histological Section (FIG. 3: Ovary)

The protocol for this manipulation is identical to that of Example 3 above. However, the samples contained in the paraffin blocks necessary for carrying out this present example are obtained from ovarian cancers originating from patients. The labeling of healthy tissue, obtained from an ovarian biopsy, by mixing an equal amount of the two MAH-II/EEL lectins (ratio 1:1) showed the absence of labeling of the cells. It can therefore be deduced from this that there are no ovarian cancer stem cells in this tissue (FIG. 3A).

In tumor tissue, several cell types coexist: tumor non-stem cells, non-tumor stem cells, tumor stem cells and non-tumor non-stem cells. The labeling of a tumor tissue by the mixture in equal quantity of MAH-II/EEL lectins (ratio 1:1) demonstrates the ability of this mixture of lectins to selectively label cancer stem cells of hormone-dependent cancer target organs, in this case to selectively mark ovarian cancer stem cells (FIG. 3B).

Example 5: Visible Labeling of Lectins on Paraffinized Histological Section (FIG. 4: Uterus)

The protocol for this manipulation is identical to those of Example 3 and of Example 4 above. However, the samples contained in the paraffin blocks necessary for carrying out this present example are obtained from cancers of the uterus originating from patients.

The labeling of healthy tissue, obtained from a uterine biopsy, by mixing an equal amount of the two MAH-II/EEL lectins (ratio 1:1) showed the absence of labeling of the cells. It can therefore be deduced from this the absence of uterine cancer stem cells in this tissue (FIG. 4A).

In tumor tissue, several cell types coexist: tumor non-stem cells, non-tumor stem cells, tumor stem cells and non-tumor non-stem cells. The labeling of a tumor tissue by the mixture in equal quantity of MAH-II/EEL lectins (ratio 1:1) demonstrates the ability of this mixture of lectins to selectively label cancer stem cells of hormone-dependent cancer target organs, in this case to selectively label uterine cancer stem cells (FIG. 4B).

The invention claimed is:

1. An in vitro method of detecting cancer stem cells of hormone-dependent cancer target organs, the method comprising contacting a biological sample with at least two labeled lectins, wherein the lectins are *Maackia amurensis lectin* II (MAH-II), and *Euonymus europaeus* lectin (EEL), and thereby labeling and detecting cancer stem cells from an organ of hormone-dependent cancer, wherein the at least two lectins are in equal amount or in a 2:1 ratio by weight, and wherein the organ is breast, uterus, or ovaries.

2. The in vitro method according to claim 1, wherein the MAH-II lectin recognizes O-linked glycans and the EEL lectin recognizes galactosylated glycans.

3. The in vitro method according to claim 2, wherein the MAH-II lectin recognizes the disialyl-T group [NeuAc α2-3Gal β1-3 (NeuAc α2-6) GalNAc].

4. The in vitro method according to claim 1, wherein the at least two labeled lectins are conjugated to a marker selected from the group consisting of rhodamine, FITC, Alexa Fluor, iodine 125, tritium, technetium, horseradish peroxidase (HRP), phosphatase alkaline, glucose oxidase β-galactosidase, gold bead, and biotin.

5. The in vitro method according to claim 1, wherein the method comprises conjugating at least two labeled lectins with a label and detecting the conjugated lectins thereby detecting the cancer stem cells of hormone-dependent cancer.

6. The in vitro method according to claim 1, wherein the method further comprises isolating said labeled cancer stem cells by magnetic beads functionalized with streptavidin or avidin in the presence of a magnet if the lectins are conjugated to biotin or by flow cytometry if the lectins are conjugated to a fluorophore.

* * * * *